(12) United States Patent  
Kleemann et al.

(10) Patent No.: US 7,317,124 B2  
(45) Date of Patent: Jan. 8, 2008

(54) ORTHO-SUBSTITUTED PENTAFLUOROSULFANYLBENZENES, PROCESS FOR THEIR PREPARATION AND THEIR USE AS VALUABLE SYNTHETIC INTERMEDIATES

(75) Inventors: Heinz-Werner Kleemann, Bischofsheim (DE); Remo Weck, Kelkheim (DE)

(73) Assignee: Sanofi-Aventis Deutschland GmbH, Frankfurt (DE)

( * ) Notice: Subject to any disclaimer, the term of this patent is extended or adjusted under 35 U.S.C. 154(b) by 139 days.

(21) Appl. No.: 10/989,027

(22) Filed: Nov. 15, 2004

(65) Prior Publication Data

US 2005/0148652 A1 Jul. 7, 2005

Related U.S. Application Data

(60) Provisional application No. 60/555,479, filed on Mar. 23, 2004.

(30) Foreign Application Priority Data

Nov. 13, 2003 (DE) ................. 103 53 205

(51) Int. Cl.
C07C 323/09 (2006.01)
C07C 255/50 (2006.01)
C07D 209/10 (2006.01)

(52) U.S. Cl. ............ 562/821; 562/824; 548/476; 558/412

(58) Field of Classification Search ......... 502/527; 562/824, 821, 826; 548/476; 558/412
See application file for complete search history.

(56) References Cited

U.S. PATENT DOCUMENTS

| | | | |
|---|---|---|---|
| 3,219,690 A * | 11/1965 | Sheppard ............ | 562/432 |
| 5,220,070 A | 6/1993 | St. Clair et al. | |
| 5,302,692 A | 4/1994 | St. Clair et al. | |
| 5,637,607 A | 6/1997 | Pilato et al. | |
| 5,741,935 A | 4/1998 | Bowden et al. | |
| 5,849,928 A | 12/1998 | Hawkins | |
| 5,851,952 A | 12/1998 | Karp et al. | |
| 5,869,426 A | 2/1999 | Karp et al. | |
| 5,965,491 A | 10/1999 | Wu et al. | |
| 6,080,861 A | 6/2000 | Karp et al. | |
| 6,096,924 A | 8/2000 | Studer et al. | |
| 6,140,528 A | 10/2000 | Hawkins | |
| 6,531,501 B1 | 3/2003 | Huber et al. | |
| 6,958,415 B2 | 10/2005 | Lal et al. | |
| 7,015,176 B2 | 3/2006 | Bailey et al. | |
| 2002/0028306 A1 | 3/2002 | Kirsch et al. | |
| 2003/0216476 A1 | 11/2003 | Kleemann | |
| 2004/0249209 A1* | 12/2004 | Bailey et al. ........... | 562/824 |
| 2005/0043401 A1* | 2/2005 | Kleemann ............... | 514/522 |
| 2005/0197370 A1* | 9/2005 | Bossenmaier et al. ...... | 514/374 |
| 2005/0202973 A1 | 9/2005 | Schaetzer et al. | |
| 2005/0215785 A1 | 9/2005 | Taylor | |

FOREIGN PATENT DOCUMENTS

| | | |
|---|---|---|
| DE | 19748109 | 6/1999 |
| DE | 10220549 | 12/2002 |
| DE | 10260474 | 7/2003 |
| DE | 10353658 | 9/2004 |
| GB | 2276379 | 9/1994 |
| GB | 2276380 | 9/1994 |
| GB | 2276381 | 9/1994 |
| WO | WO94/21606 | 9/1994 |
| WO | WO94/22817 | 10/1994 |
| WO | WO95/16676 | 6/1995 |
| WO | WO96/25401 | 8/1996 |
| WO | WO 9705106 A1 * | 2/1997 |
| WO | WO 9922857 A1 * | 5/1999 |
| WO | WO99/47139 | 9/1999 |
| WO | WO02/28182 | 4/2002 |
| WO | WO03/093228 | 11/2003 |
| WO | WO2005/019377 | 3/2005 |
| WO | WO2005/019378 | 3/2005 |
| WO | WO2005/021488 | 3/2005 |

(Continued)

OTHER PUBLICATIONS

Bowden, R. et al., A New Method for the Synthesis of Aromatic Sulfurpentafluorides and Studies of the Stability of the Sulfurpentafluoride Group in Common Synthetic Transformations, Tetrahedron 2000, vol. 56 pp. 3399-3408.

Kirsch, P. et. al., Liquid Crystals Based on Hypervalent Sulfur Flurides: Pentafluorosulfuranyl as Polar Terminal Group, Angew. Chem. Int. Ed. 1999, vol. 38, pp. 1989-1992.

(Continued)

Primary Examiner—Rebecca Anderson
Assistant Examiner—Karen Cheng
(74) Attorney, Agent, or Firm—Joseph D. Rossi; Robert J. Kajubi

(57) ABSTRACT

Pentafluorosulfanyl-benzenes according to Formula (I):

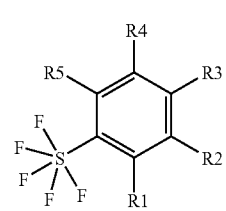

a process for their preparation and their use as valuable synthetic intermediates for preparing, for example, medicaments, diagnostic aids, liquid crystals, polymers, pesticides, herbicides, fungicides, nematicides, parasiticides, insecticides, acaricides and arthropodicides.

3 Claims, No Drawings

FOREIGN PATENT DOCUMENTS

| WO | WO2005047239 A1 | * | 5/2005 |
| WO | WO 2005047241 A1 | * | 5/2005 |
| WO | WO2005/051390 | | 6/2005 |

OTHER PUBLICATIONS

Kirsch, P. et. al., Nematic Liquid Crystals for Active Matrix Displays: Molecular Design and Synthesis, Agnew, Chem. Int. Ed. 2000, vol. 39, pp. 4216-4235.

Larock, R, Comprehensive Organic Transformations: A Guide to Functional Group Preparations Second Edition, Wiley-VCH Publishers, New York, Weinheim 1999, pp. 821-828.

Larock, R., Comprehensive Organic Transformations: A Guide to Functional Group Preparations Second Edition, Wiley-VCH Publishers, New York, Weinheim 1999, pp. 619-628.

Mohand, S. et. al., New and Convenient Method for Incorparation of Pentafluorosulfanyl (SFS) Substituents Into Aliphatic Organic Compounds, Organic Letters 2002, vol. 4, No. 17 pp. 3013-3015.

Sheppard William A., Arylsulfur Pentafluorides, Journal of the American Chemical Society; vol. 84; No. 16; (Aug. 20, 1962); pp. 3064-3072.

Sipyagin, A. et. al., Preparation of the First Ortho-Substituted Pentafluorosulfanylbenzenes, Journal of Fluorine Chemistry 2001, vol. 112 pp. 287-295.

* cited by examiner

ORTHO-SUBSTITUTED PENTAFLUOROSULFANYLBENZENES, PROCESS FOR THEIR PREPARATION AND THEIR USE AS VALUABLE SYNTHETIC INTERMEDIATES

RELATED APPLICATIONS

This Application is based on and claims priority under 35 U.S.C. § 119(e) from U.S. provisional patent application Ser. No. 60/555,479, filed on Mar. 23, 2004, which is incorporated herein by reference. This Application is also based on and claims priority under 35 U.S.C. § 119(a) from Federal Republic of Germany patent application No. 10353205.6, filed on Nov. 13, 2003, which is incorporated herein by reference.

FIELD OF THE INVENTION

This Application relates to ortho-substituted pentafluorosulfanylbenzenes, according to Formula (I), a process for their preparation and their use as valuable synthetic intermediates for preparing, for example, medicaments, diagnostic aids, liquid crystals, polymers, pesticides, herbicides, fungicides, nematicides, parasiticides, insecticides, acaricides and arthropodicides.

BACKGROUND OF THE INVENTION

The chemistry of pentafluorosulfanyl derivatives has gained importance in the last few years, especially since novel preparation processes have been found (Tetrahedron 56 (2000) 3399; Organic Letters 4(17) (2002) 3013). However, to date only very few compounds are known which bear substituents other than hydrogen and fluorine on a phenyl ring in the ortho-position to the pentafluorosulfanyl group. The only known synthetic route (Journal of Fluorine Chemistry 112 (2001) 287) uses expensive reagents such as $AgF_2$ and is afflicted with poor yields. The authors account for this by the large bulk of the pentafluorosulfanyl group which generally makes ortho-substitution very difficult. This opinion is also shared by other authors (J. Am. Chem. Soc. 84 (1962) 3064).

SUMMARY OF THE INVENTION

In one aspect, the present invention relates to pentafluorosulfanylbenzenes according to Formula (I):

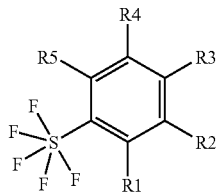

I wherein:
R1 is:
(a) Cl, Br, I, —CN, —SO$_2$R6, NO$_2$, alkoxy having 1 to 4 carbon atoms, NR7R8, —O—(CH$_2$)$_b$—(CF$_2$)$_c$—CF$_3$, —(SO$_d$)$_e$—(CH$_2$)$_f$—(CF$_2$)$_g$—CF$_3$, alkyl having 1 to 6 carbon atoms or cycloalkyl having 3 to 8 carbon atoms, wherein 1 to 4 hydrogen atoms in said alkyl or cycloalkyl may be replaced by fluorine atoms, where a, b and c are, each independently, 0 to 1, d is 0 to 2, e is 0 to 1, f is 0 to 4, and g is 0 to 1; and where
R6 is OH, F, Cl, Br, I or alkyl having 1 to 4 carbon atoms; and
R7 and R8 are, each independently, hydrogen, —CH$_2$—CF$_3$, or alkyl having 1 to 4 carbon atoms; or (b) —(CH$_2$)$_h$-phenyl or —O-phenyl, wherein the phenyl radicals are unsubstituted or substituted by 1 to 3 radicals selected, each independently, from the group consisting of F, Cl, Br, I, —O$_j$—(CH$_2$)$_k$—CF$_3$, —SO$_2$CH$_3$, alkoxy having 1 to 4 carbon atoms, and alkyl having 1 to 4 carbon atoms, where j is 0 to 1, k is 0 to 3, and h is 0 to 4; or (c) —(CH$_2$)$_l$-heteroaryl which is unsubstituted or substituted by 1 to 3 radicals selected, each independently, from the group consisting of F, Cl, Br, I, —O$_m$—(CH$_2$)$_n$—CF$_3$, —SO$_2$CH$_3$, alkoxy having 1 to 4 carbon atoms, and alkyl having 1 to 4 carbon atoms, where m is 0 to 1, n is 0 to 3, and l is 0 to 4;

R2 and R4 are, each independently, hydrogen, F, Cl, Br, I, —CN, NR9R10, —OR11, —SR12, —COR13, —SO$_q$CH$_3$, —(SO$_r$)$_s$—(CH$_2$)$_t$—(CF$_2$)$_u$—CF$_3$, alkyl having 1 to 6 carbon atoms, or cycloalkyl having 3 to 8 carbon atoms, wherein 1 to 4 hydrogen atoms in said alkyl or cycloalkyl may be replaced by fluorine atoms, where q and r are, each independently, 1 to 2, s is 0 to 1, t is 0 to 4, u is 0 to 1; and where R9 and R10:
(a) are each independently, —(CH$_2$)$_v$—(CF$_2$)$_w$—CF$_3$, alkyl having 1 to 4 carbon atoms, alkylcarbonyl having 1 to 4 carbon atoms, or alkylsulfonyl having 1 to 4 carbon atoms, where v is 0 to 1 and w is 0 to 1; or
(b) together with the nitrogen atom bearing them, form a heterocycle of Formula (III):

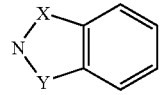

III where X and Y are, each independently, CO or SO$_2$; and where

R11 and R12 are, each independently, hydrogen, —(CH$_2$)$_v$—(CF$_2$)$_w$—CF$_3$, alkyl having 1 to 4 carbon atoms, alkylcarbonyl having 1 to 4 carbon atoms, or alkylsulfonyl having 1 to 4 carbon atoms where v is 0 to 1 and w is 0 to 1; and R13 is OH, alkyl having 1 to 6 carbon atoms or alkoxy having 1 to 6 carbon atoms;

R3 is hydrogen, F, Cl, Br, I, —CN, —NO$_2$, —COR14, —SO$_2$CH$_3$, —O$_x$—(CH$_2$)$_y$—CF$_3$, alkyl having 1 to 6 carbon atoms, or alkoxy having 1 to 4 carbon atoms, where x is 0 to 1 and y is 0 to 3; and where R14 is OH, —O$_{aa}$—(CH$_2$)$_{bb}$—CF$_3$, alkyl having 1 to 6 carbon atoms, or alkoxy having 1 to 6 carbon atoms, where aa is 0 to 1 and bb is 0 to 3;

R5 is:
(a) hydrogen, F, Cl, Br, I, —CN, —SO$_2$CH$_3$, NR15R16, —O—(CH$_2$)$_{ee}$—(CF$_2$)$_{ff}$—CF$_3$, —(SO$_{gg}$)$_{hh}$—(CH$_2$)$_{jj}$—(CF$_2$)$_{kk}$—CF$_3$, alkoxy having 1 to 4 carbon atoms, alkyl having 1 to 6 carbon atoms or cycloalkyl having 3 to 8 carbon atoms, where 1 to 4 hydrogen atoms in said alkyl or cycloalkyl may be replaced by fluorine atoms, where ee and ff are, each independently, 0 to 1, gg is 0 to 2, hh is 0 to 1, jj is 0 to 4, kk is 0 to 1; and where R15 and R16 are, each independently, hydrogen, —CH$_2$—CF$_3$, alkyl having 1 to 4 carbon atoms; or (b) —(CH$_2$)$_{ll}$-phenyl or —O-phenyl, wherein the phenyl radicals are unsubstituted or substituted by 1 to 3 radicals selected, each independently, from the group consisting of F, Cl, Br, I, —SO$_2$CH$_3$, —O$_{mm}$—(CH$_2$)$_{nn}$—CF$_3$, alkoxy having 1 to 4 carbon atoms, or alkyl having 1 to 4 carbon atoms, where mm is 0 to 1, nn is 0 to 3, and ll is 0 to 4; or (c) —(CH$_2$)$_{oo}$-heteroaryl which is unsubstituted or substituted by 1 to 3 radicals selected, each independently, from the group consisting of F, Cl, Br, I, —SO$_2$CH$_3$, —O$_{pp}$—(CH$_2$)$_{rr}$, —CF$_3$, alkoxy having 1 to 4 carbon atoms or alkyl having 1 to 4 carbon atoms, where pp is 0 to 1, rr is 0 to 3, and oo is 0 to 4;

or a salt of a compound of Formula (I), excluding compounds of Formula (I) and the corresponding salts wherein, in the same molecule:

R2 and R4 are each Cl and R3 is F or Cl;

R2 and R4 are either Cl or CN, wherein R2 and R4 have a total of one Cl and one CN substituent, and R3 is Cl; and R1 is NO$_2$ and the other substituents are each hydrogen.

In one embodiment, preference is given to compounds of Formula (I) wherein:

R1 is:
(a) Cl, Br, I, —CN, —SO$_2$R6, NO$_2$, alkoxy having 1 to 4 carbon atoms, NR7R8, —O—(CH$_2$)$_b$—(CF$_2$)$_c$—CF$_3$, —(SO$_d$)$_e$—(CH$_2$)$_f$—(CF$_2$)$_g$—CF$_3$, alkyl having 1 to 6 carbon atoms or cycloalkyl having 3 to 8 carbon atoms, wherein 1 to 4 hydrogen atoms in said alkyl or cycloalkyl may be replaced by fluorine atoms; where a, b and c are, each independently, 0 to 1, d is 0 to 2, e is 0 to 1, f is 0 to 4, and g is 0 to 1; and where R6 is OH, F, Cl, Br, I or alkyl having 1 to 4 carbon atoms; and R7 and R8 are, each independently, hydrogen, —CH$_2$—CF$_3$, or alkyl having 1 to 4 carbon atoms; or (b) —(CH$_2$)$_h$-phenyl or —O-phenyl, wherein the phenyl radicals are unsubstituted or substituted by 1 to 3 radicals selected, each independently, from the group consisting of F, Cl, Br, I, —O$_j$—(CH$_2$)$_k$—CF$_3$, —SO$_2$CH$_3$, alkoxy having 1 to 4 carbon atoms, and alkyl having 1 to 4 carbon atoms, where j is 0 to 1, k is 0 to 3, and h is 0 to 4; or (c) —(CH$_2$)$_l$-heteroaryl which is unsubstituted or substituted by 1 to 3 radicals selected, each independently, from the group consisting of F, Cl, Br, I, —O$_m$—(CH$_2$)$_n$—CF$_3$, —SO$_2$CH$_3$, alkoxy having 1 to 4 carbon atoms, and alkyl having 1 to 4 carbon atoms, where m is 0 to 1, n is 0 to 3, and l is 0 to 4;

R2 and R4 are, each independently, hydrogen, F, Cl, Br, I, —CN, NR9R10, —OR11, —SR12, —COR13, —(SO$_r$)$_s$—(CH$_2$)$_t$—(CF$_2$)$_u$—CF$_3$, alkyl having 1 to 6 carbon atoms, or cycloalkyl having 3 to 8 carbon atoms, wherein 1 to 4 hydrogen atoms in said alkyl or cycloalkyl may be replaced by fluorine atoms, where q and r are, each independently, 1 to 2, s is 0 to 1, t is 0 to 1, u is 0 to 1; and where R9 and R10:
(a) are each independently, —(CH$_2$)$_v$—(CF$_2$)$_w$—CF$_3$, alkyl having 1 to 4 carbon atoms, alkylcarbonyl having 1 to 4 carbon atoms, or alkylsulfonyl having 1 to 4 carbon atoms, where v is 0 to 1 and w is 0 to 1; or (b) together with the nitrogen atom bearing them, form a heterocycle of Formula (III):

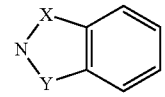

III where X and Y are, each independently, CO or SO$_2$; and where

R11 and R12 are, each independently, hydrogen, —(CH$_2$)$_v$—(CF$_2$)$_w$—CF$_3$, alkyl having 1 to 4 carbon atoms, alkylcarbonyl having 1 to 4 carbon atoms, or alkylsulfonyl having 1 to 4 carbon atoms where v is 0 to 1 and w is 0 to 1; and R13 is OH, alkyl having 1 to 6 carbon atoms or alkoxy having 1 to 6 carbon atoms;

R3 is hydrogen, F, Cl, Br, I, —CN, —NO$_2$, —COR14, —SO$_2$CH$_3$, —O$_x$—(CH$_2$)$_y$—CF$_3$, alkyl having 1 to 6 carbon atoms, or alkoxy having 1 to 4 carbon atoms, where x is 0 to 1 and y is 0 to 3; and where R14 is OH, —O$_{aa}$—(CH$_2$)$_{bb}$—CF$_3$, alkyl having 1 to 6 carbon atoms, or alkoxy having 1 to 6 carbon atoms, where aa is 0 to 1 and bb is 0 to 3;

or a salt of a compound of Formula (I), excluding compounds of Formula (I) and the corresponding salts wherein, in the same molecule:

R2 and R4 are each Cl and R3 is F or Cl;

R2 and R4 are either Cl or CN, wherein R2 and R4 have a total of one Cl and one CN substituent, and R3 is Cl; and R1 is NO$_2$ and the other substituents are each hydrogen.

In another embodiment, preference is given to compounds of Formula (I) wherein:

R1 is Cl, Br, I, —SO$_2$R6 or NO$_2$; and where
R6 is OH, F, Cl, Br, I or alkyl having 1 to 4 carbon atoms;

R2 and R4 are, each independently, hydrogen, F, Cl, Br, I, —CN,

NR9R10, —OR11, —SR12, —COR13, —(SO$_r$)$_s$—(CH$_2$)$_t$—(CF$_2$)$_u$—CF$_3$, alkyl having 1 to 6 carbon atoms, or cycloalkyl having 3 to 8 carbon atoms, wherein 1 to 4 hydrogen atoms in said alkyl or cycloalkyl may be replaced by fluorine atoms, where r is 1 to 2, s is 0 to 1, t is 0 to 1, u is 0 to 1; and where R9 and R10:
(a) are each independently, —(CH$_2$)$_v$—(CF$_2$)$_w$—CF$_3$, alkyl having 1 to 4 carbon atoms, alkylcarbonyl having 1 to 4 carbon atoms, or alkylsulfonyl having 1 to 4 carbon atoms, where v is 0 to 1 and w is 0 to 1; or (b) together with the nitrogen atom bearing them, form a heterocycle of Formula (IIIa):

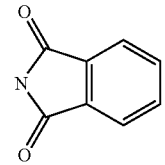

IIIa

R11 and R12 are, each independently, hydrogen, —$(CH_2)_v$—$(CF_2)_w$—$CF_3$, alkyl having 1 to 4 carbon atoms, alkylcarbonyl having 1 to 4 carbon atoms, or alkylsulfonyl having 1 to 4 carbon atoms where v is 0 to 1 and w is 0 to 1; and R13 is OH, alkyl having 1 to 6 carbon atoms or alkoxy having 1 to 6 carbon atoms;

R3 is hydrogen, F, Cl, Br, I, —CN, —$NO_2$, —COR14, —$SO_2CH_3$, —$O_x$—$(CH_2)_y$—$CF_3$, alkyl having 1 to 6 carbon atoms, or alkoxy having 1 to 4 carbon atoms, where x is 0 to 1 and y is 0 to 3; and where R14 is OH, —$O_{aa}$—$(CH_2)_{bb}$—$CF_3$, alkyl having 1 to 6 carbon atoms, or alkoxy having 1 to 6 carbon atoms, where aa is 0 to 1 and bb is 0 to 3;

or a salt of a compound of Formula (I), excluding compounds of Formula (I) and the corresponding salts wherein, in the same molecule:

R2 and R4 are each Cl and R3 is F or Cl;

R2 and R4 are either Cl or CN, wherein R2 and R4 have a total of one Cl and one CN substituent, and R3 is Cl; and R1 is $NO_2$ and the other substituents are each hydrogen.

In one embodiment, preference is given to compounds of Formula (I) wherein:

R1 is:
(a) Cl, Br, I, —CN, —$SO_2R6$, $NO_2$, alkoxy having 1 to 4 carbon atoms, NR7R8, —O—$(CH_2)_b$—$(CF_2)_c$—$CF_3$, —$(SO_d)_e$—$(CH_2)_f$—$(CF_2)_g$—$CF_3$, alkyl having 1 to 6 carbon atoms or cycloalkyl having 3 to 8 carbon atoms, wherein 1 to 4 hydrogen atoms in said alkyl or cycloalkyl may be replaced by fluorine atoms, where a, b and c are, each independently, 0 to 1, d is 0 to 2, e is 0 to 1, f is 0 to 4, and g is 0 to 1; and where R6 is OH, F, Cl, Br, I or alkyl having 1 to 4 carbon atoms; and R7 and R8 are, each independently, hydrogen, —$CH_2$—$CF_3$, or alkyl having 1 to 4 carbon atoms; or (b) —$(CH_2)_h$-phenyl or —O-phenyl, wherein the phenyl radicals are unsubstituted or substituted by 1 to 3 radicals selected, each independently, from the group consisting of F, Cl, Br, I, —$O_j$—$(CH_2)_k$—$CF_3$, —$SO_2CH_3$, alkoxy having 1 to 4 carbon atoms, and alkyl having 1 to 4 carbon atoms, where j is 0 to 1, k is 0 to 3, and h is 0 to 4; or (c) —$(CH_2)_l$-heteroaryl which is unsubstituted or substituted by 1 to 3 radicals selected, each independently, from the group consisting of F, Cl, Br, I, —$O_m$—$(CH_2)_n$—$CF_3$, —$SO_2CH_3$, alkoxy having 1 to 4 carbon atoms, and alkyl having 1 to 4 carbon atoms, where m is 0 to 1, n is 0 to 3, and l is 0 to 4;

R2 and R4 are, each independently, hydrogen, F, Cl, Br, I, —CN, NR9R10, —OR11, —SR12, —COR13, —$SO_qCH_3$, —$(SO_r)_s$—$(CH_2)_t$—$(CF_2)_u$—$CF_3$, alkyl having 1 to 6 carbon atoms, or cycloalkyl having 3 to 8 carbon atoms, wherein 1 to 4 hydrogen atoms in said alkyl or cycloalkyl may be replaced by fluorine atoms, where q and r are, each independently, 1 to 2, s is 0 to 1, t is 0 to 1, u is 0 to 1; and where R9, R10, R11 and R12 are, each independently, hydrogen, —$(CH_2)_v$—$(CF_2)_w$—$CF_3$, alkyl having 1 to 4 carbon atoms, alkylcarbonyl having 1 to 4 carbon atoms, or alkylsulfonyl having 1 to 4 carbon atoms, where v and w are, each independently, 0 to 1; and where R13 is OH, alkyl having 1 to 6 carbon atoms or alkoxy having 1 to 6 carbon atoms;

R3 is hydrogen, F, Cl, Br, I, —CN, —$NO_2$, —COR14, —$SO_2CH_3$, —$O_x$—$(CH_2)_y$—$CF_3$, alkyl having 1 to 6 carbon atoms, or alkoxy having 1 to 4 carbon atoms, where x is 0 to 1 and y is 0 to 3; and where R14 is OH, —$O_{aa}$—$(CH_2)_{bb}$—$CF_3$, alkyl having 1 to 6 carbon atoms, or alkoxy having 1 to 6 carbon atoms, where aa is 0 to 1 and bb is 0 to 3;

R5 is:
(a) hydrogen, F, Cl, Br, I, —CN, —$SO_2CH_3$, NR15R16, —O—$(CH_2)_{ee}$—$(CF_2)_{ff}$—$CF_3$, —$(SO_{gg})_{hh}$—$(CH_2)_{jj}$—$(CF_2)_{kk}$—$CF_3$, alkyl having 1 to 6 carbon atoms or cycloalkyl having 3 to 8 carbon atoms, where 1 to 4 hydrogen atoms in said alkyl or cycloalkyl may be replaced by fluorine atoms, where ee and ff are, each independently, 0 to 1, gg is 0 to 2, hh is 0 to 1, jj is 0 to 4, kk is 0 to 1; and where R15 and R16 are, each independently, hydrogen, —$CH_2$—$CF_3$, alkyl having 1 to 4 carbon atoms; or (b) —$(CH_2)_{ll}$-phenyl or —O-phenyl, wherein the phenyl radicals are unsubstituted or substituted by 1 to 3 radicals selected, each independently, from the group consisting of F, Cl, Br, I, —$SO_2CH_3$, —$O_{mm}$—$(CH_2)_{nn}$—$CF_3$, alkoxy having 1 to 4 carbon atoms, or alkyl having 1 to 4 carbon atoms, where mm is 0 to 1, nn is 0 to 3, and ll is 0 to 4; or (c) —$(CH_2)_{oo}$-heteroaryl which is unsubstituted or substituted by 1 to 3 radicals selected, each independently, from the group consisting of F, Cl, Br, I, —$SO_2CH_3$, —$O_{pp}$—$(CH_2)_{rr}$—$CF_3$, alkoxy having 1 to 4 carbon atoms or alkyl having 1 to 4 carbon atoms, where pp is 0 to 1, rr is 0 to 3, and oo is 0 to 4;

or a salt of a compound of Formula (I), excluding compounds of Formula (I) and the corresponding salts wherein, in the same molecule:

R1 and R4 are each $NH_2$ and R2, R3 and R5 are each hydrogen;

R2 and R4 are each Cl and R3 is F or Cl; and

R2 and R4 are either Cl or CN, wherein R2 and R4 have a total of one CL and one

CN substituent, and R3 is Cl.

In one embodiment, preference is given to compounds of Formula (I) where R1 is Cl, Br, I, —$SO_2R6$ where R6 is OH, F, Cl, Br, I or alkyl having 1 to 4 carbon atoms, or —$NO_2$.

In another embodiment, preference is given to compounds wherein R1 is Cl, Br, I, —$SO_2R6$, where R6 is OH or Cl, or —$NO_2$.

In another embodiment, preference is given to compounds of Formula (I) wherein R1 is Cl or $NO_2$.

In another embodiment, preference is given to compounds of Formula (I) wherein R1 is $NO_2$.

In a further embodiment, preference is given to compounds of Formula (I) wherein R1 is Cl, Br, I, —$SO_2R6$ where R6 is OH or Cl.

In a further embodiment, preference is given to compounds of Formula(I) wherein R2 and R4 are, each independently, hydrogen, F, Cl, Br, I, —CN, NR9R10, —OR11, —SR12, —COR13, —$SO_qCH_3$, —$(SO_r)_s$—$(CH_2)_t$—$(CF_2)_u$—$CF_3$, alkyl having 1 to 6 carbon atoms, or cycloalkyl having 3 to 8 carbon atoms, wherein 1 to 4 hydrogen atoms in said alkyl or cycloalkyl may be replaced by fluorine atoms, where q and r are, each independently, 1 to 2, s is 0 to 1, t is 0 to 1, u is 0 to 1; and where R9 and R10:
(a) are each independently, —$(CH_2)_v$—$(CF_2)_w$—$CF_3$, alkyl having 1 to 4 carbon atoms, alkylcarbonyl having 1 to 4 carbon atoms, or alkylsulfonyl having 1 to 4 carbon atoms, where v is 0 to 4 and w is 0 to 1; or (b) together with the nitrogen atom bearing them, form a heterocycle of Formula (III):

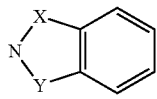

III where X and Y are, each independently, CO or $SO_2$; and where

R11 and R12 are, each independently, hydrogen, —$(CH_2)_v$—$(CF_2)_w$—$CF_3$, alkyl having 1 to 4 carbon atoms, alkylcarbonyl having 1 to 4 carbon atoms, or alkylsulfonyl having 1 to 4 carbon atoms where v is 0 to 1 and w is 0 to 1; and R13 is OH, alkyl having 1 to 6 carbon atoms or alkoxy having 1 to 6 carbon atoms.

In another embodiment, preference is given to compounds wherein R2 and R4 are, each independently, described by hydrogen, NR9R10 and COR13, where R9 and R10 are, each independently, alkylcarbonyl having 1 to 4 carbon atoms, for example methylcarbonyl, or R9 and R10, together with the nitrogen atom which bears them, form a heterocycle of Formula (II),

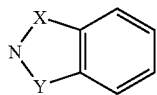

III wherein X and Y are, each independently, described by CO or $SO_2$;

For example, R9 and R10, together with the nitrogen atom which bears them, may form a heterocycle of Formula (IIIa):

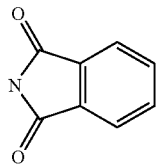

IIIa and where R13 is alkoxy having 1 to 6 carbon atoms, for example methoxy.

In a further embodiment, one of the R2 and R4 radicals in the compounds of Formula (I) is hydrogen.

In a further embodiment, preference is given to compounds of Formula (I) wherein R3 is hydrogen, F, Cl, Br, I, —CN or —COR14 where R14 is OH or alkoxy having 1 to 6 carbon atoms, for example methoxy.

In another embodiment, preference is given to compounds of Formula (I) wherein R3 is hydrogen, CN or $COOCH_3$.

In a further embodiment, preference is given to compounds of Formula (I) wherein R5 is hydrogen or F.

In another embodiment, preference is given to compounds of Formula (I) wherein R5 is hydrogen.

Radicals which occur more than once may be the same or different and, each independently, have the definitions specified.

When the substituents R1 to R5 contain one or more centers of asymmetry, they may, each independently, have either the S or the R configuration. The compounds may be in the form of optical isomers, of diastereomers, of racemates or of mixtures thereof in all ratios.

The present invention encompasses all tautomeric forms of the compounds of Formula (I), and their pharmaceutically acceptable salts.

Alkyl radicals may be straight-chain or branched. This also applies if they bear substituents or occur as substituents of other radicals, for example in fluoroalkyl radicals or alkoxy radicals. Examples of alkyl radicals are methyl, ethyl, n-propyl, isopropyl(=1-methylethyl), n-butyl, isobutyl (=2-methylpropyl), sec-butyl(=1-methylpropyl), tert-butyl (=1,1-dimethylethyl), n-pentyl, isopentyl, tert-pentyl, neopentyl and hexyl. In one embodiment, preferred alkyl radicals include methyl, ethyl, n-propyl and isopropyl. One or more, for example 1, 2, 3, 4 or 5, hydrogen atoms in alkyl radicals may be replaced by fluorine atoms. Examples of such fluoroalkyl radicals are trifluoromethyl, 2,2,2-trifluoroethyl and pentafluoroethyl. Substituted alkyl radicals may be substituted in any positions.

Examples of cycloalkyl radicals are cyclopropyl, cyclobutyl, cyclopentyl, cyclohexyl, cycloheptyl or cyclooctyl. In cycloalkyl radicals, one or more, for example 1 to 4, hydrogen atoms may be replaced by fluorine atoms. Substituted cycloalkyl radicals may be substituted in any positions.

Phenyl radicals may be unsubstituted or be mono- or polysubstituted, for example mono-, di- or trisubstituted, by identical or different radicals. In one embodiment, when a phenyl radical is substituted, it preferably has one or two identical or different substituents. The above characteristics of phenyl radicals likewise apply to substituted phenyl radicals, such as, for example, phenylalkyl or phenyloxy. In monosubstituted phenyl radicals, the substituent may be in the 2-position, 3-position or 4-position. Disubstituted phenyl may be substituted in the 2,3-position, 2,4-position, 2,5-position, 2,6-position, 3,4-position or 3,5-position. The substituents in trisubstituted phenyl radicals may be in the 2,3,4-position, 2,3,5-position, 2,4,5-position, 2,4,6-position, 2,3,6-position or 3,4,5-position.

Heteroaryl radicals are aromatic ring compounds wherein one or more ring atoms are oxygen atoms, sulfur atoms or nitrogen atoms, for example 1 to 3 nitrogen atoms, 1 to 2 oxygen atoms, 1 to 2 sulfur atoms or a combination of different heteroatoms. The heteroaryl radicals may be attached via all positions, for example via the 1-position, 2-position, 3-position, 4-position, 5-position, 6-position, 7-position or 8-position. Heteroaryl radicals may be unsubstituted or be mono- or polysubstituted, for example mono-, di- or trisubstituted, by identical or different radicals. This applies likewise to heteroaryl radicals bound to other functional moieties, for example the heteroarylalkyl radical. Examples of heteroaryl are furanyl, thienyl, pyrrolyl, imidazolyl, pyrazolyl, triazolyl, tetrazolyl, oxazolyl, isoxazolyl, thiazolyl, isothiazolyl, pyridyl, pyrazinyl, pyrimidinyl, pyridazinyl, indolyl, indazolyl, quinolyl, isoquinolyl, phthalazinyl, quinoxalinyl, quinazolinyl and cinnolinyl.

Further examples of heteroaryl radicals include 2- or 3-thienyl, 2- or 3-furyl, 1-, 2- or 3-pyrrolyl, 1-, 2-, 4- or 5-imidazolyl, 1-, 3-, 4- or 5-pyrazolyl, 1,2,3-triazol-1-, -4- or -5-yl, 1,2,4-triazol-1-, -3- or -5-yl, 1- or 5-tetrazolyl, 2-, 4- or 5-oxazolyl, 3-, 4- or 5-isoxazolyl, 1,2,3-oxadiazol-4- or -5-yl, 1,2,4-oxadiazol-3- or -5-yl, 1,3,4-oxadiazol-2-yl or -5-yl, 2-, 4- or 5-thiazolyl, 3-, 4- or 5-isothiazolyl, 1,3,4-thiadiazol-2- or -5-yl, 1,2,4-thiadiazol-3- or -5-yl, 1,2,3-thiadiazol-4- or -5-yl, 2-, 3- or 4-pyridyl, 2-, 4-, 5- or 6-pyrimidinyl, 3- or 4-pyridazinyl, 2- or 3-pyrazinyl, 1-, 2-, 3-, 4-, 5-, 6- or 7-indolyl, 1-, 2-, 4- or 5-benzimidazolyl, 1-, 3-, 4-, 5-, 6- or 7-indazolyl, 2-, 3-, 4-, 5-, 6-, 7- or 8-quinolyl, 1-, 3-, 4-, 5-, 6-, 7- or 8-isoquinolyl, 2-, 4-, 5-, 6-, 7- or 8-quinazolinyl, 3-, 4-, 5-, 6-, 7- or 8-cinnolinyl, 2-, 3-, 5-, 6-, 7- or 8-quinoxalinyl, 1-, 4-, 5-, 6-, 7- or 8-phthalazinyl. Also included are the corresponding N-oxides of these compounds, for example 1-oxy-2-, -3- or -4-pyridyl.

In one embodiment, preferred heteroaromatic radicals include 2- or 3-thienyl, 2- or 3-furyl, 1-, 2- or 3-pyrrolyl, 1-, 2-, 4- or 5-imidazolyl, 2-, 3-, 4-, 5-, 6-, 7- or 8-quinolyl, 1-, 3-, 4- or 5-pyrazolyl, 2-, 3- or 4-pyridyl, 2- or 3-pyrazinyl, 2-, 4-, 5- or 6-pyrimidinyl and 3- or 4-pyridazinyl.

Other than in the operating examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The invention further relates to a process for preparing an ortho-substituted pentafluorosulfanylbenzene comprising reacting a pentafluorosulfanylbenzene with a nucleophile or organometallic compound effective to ortho-substitute said pentafluorosulfanyl benzene with a substituent defined by the group R1, wherein:

R1 is:
(a) Cl, Br, I, —CN, —$SO_2R6$, $NO_2$, alkoxy having 1 to 4 carbon atoms, NR7R8, —O—$(CH_2)_b$—$(CF_2)_c$—$CF_3$, —$(SO_d)_e$—$(CH_2)_f$—$(CF_2)_g$—$CF_3$, alkyl having 1 to 6 carbon atoms or cycloalkyl having 3 to 8 carbon atoms, wherein 1 to 4 hydrogen atoms in said alkyl or cycloalkyl may be replaced by fluorine atoms; where a, b and c are, each independently, 0 to 1, d is 0 to 2, e is 0 to 1, f is 0 to 4, and g is 0 to 1; and where
R6 is OH, F, Cl, Br, I or alkyl having 1 to 4 carbon atoms; and
R7 and R8 are, each independently, —$CH_2$—$CF_3$, hydrogen, or alkyl having 1 to 4 carbon atoms; or
(b) —$(CH_2)_h$-phenyl or —O-phenyl, wherein the phenyl radicals are unsubstituted or substituted by 1 to 3 radicals selected, each independently, from the group consisting of F, Cl, Br, I, —$O_j$—$(CH_2)_k$—$CF_3$, —$SO_2CH_3$, alkoxy having 1 to 4 carbon atoms, and alkyl having 1 to 4 carbon atoms, where j is 0 to 1, k is 0 to 3, and h is 0 to 4; or
(c) —$(CH_2)_i$-heteroaryl which is unsubstituted or substituted by 1 to 3 radicals selected, each independently, from the group consisting of F, Cl, Br, I, —$O_m$—$(CH_2)_n$—$CF_3$, —$SO_2CH_3$, alkoxy having 1 to 4 carbon atoms, and alkyl having 1 to 4 carbon atoms, where m is 0 to 1, n is 0 to 3, and l is 0 to 4;

R2 and R4 are, each independently, hydrogen, F, Cl, Br, I, —CN, NR9R10, —OR11, —SR12, —COR13, —$SO_q$$CH_3$, —$(SO_r)_s$—$(CH_2)_t$—$(CF_2)_u$—$CF_3$, alkyl having 1 to 6 carbon atoms, or cycloalkyl having 3 to 8 carbon atoms, wherein 1 to 4 hydrogen atoms in said alkyl or cycloalkyl may be replaced by fluorine atoms, where q and r are, each independently, 1 to 2, s is 0 to 1, t is 0 to 1, u is 0 to 1; and where R9 and R10:
(a) are each independently, —$(CH_2)_v$—$(CF_2)_w$—$CF_3$, alkyl having 1 to 4 carbon atoms, alkylcarbonyl having 1 to 4 carbon atoms, or alkylsulfonyl having 1 to 4 carbon atoms, where v is 0 to 1 and w is 0 to 1; or
(b) together with the nitrogen atom bearing them, form a heterocycle of Formula (III):

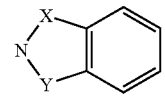

where X and Y are, each independently, CO or $SO_2$; and where

R11 and R12 are, each independently, —$(CH_2)_v$—$(CF_2)_w$—$CF_3$, hydrogen, alkyl having 1 to 4 carbon atoms, alkylcarbonyl having 1 to 4 carbon atoms, or alkylsulfonyl having 1 to 4 carbon atoms where v is 0 to 1 and w is 0 to 1; and R13 is OH, alkyl having 1 to 6 carbon atoms or alkoxy having 1 to 6 carbon atoms;

R3 is hydrogen, F, Cl, Br, I, —CN, —$NO_2$, —COR14, —$SO_2CH_3$, alkyl having 1 to 6 carbon atoms, alkoxy having 1 to 4 carbon atoms, or —$O_x$—$(CH_2)_y$—$CF_3$, where x is 0 to 1 and y is 0 to 3; and where R14 is OH, alkyl having 1 to 6 carbon atoms, alkoxy having 1 to 6 carbon atoms or —$O_{aa}$—$(CH_2)_{bb}$—$CF_3$, where aa is 0 to 1 and bb is 0 to 3;

R5 is:
(a) hydrogen, F, Cl, Br, I, —CN, —$SO_2CH_3$, NR15R16, —O—$(CH_2)_{ee}$—$(CF_2)_{ff}$—$CF_3$, —$(SO_{gg})_{hh}$—$(CH_2)_{jj}$—$(CF_2)_{kk}$—$CF_3$, alkoxy having 1 to 4 carbon atoms, alkyl having 1 to 6 carbon atoms or cycloalkyl having 3 to 8 carbon atoms, where 1 to 4 hydrogen atoms in said alkyl or cycloalkyl may be replaced by fluorine atoms, where ee and ff are, each independently, 0 to 1, gg is 0 to 2, hh is 0 to 1, jj is 0 to 4, kk is 0 to 1; and where
R15 and R16 are, each independently, hydrogen, —$CH_2$—$CF_3$, alkyl having 1 to 4 carbon atoms; or
(b) —$(CH_2)_{ll}$-phenyl or —O-phenyl, wherein the phenyl radicals are unsubstituted or substituted by 1 to 3 radicals selected, each independently, from the group consisting of F, Cl, Br, I, —$SO_2CH_3$, —$O_{mm}$—$(CH_2)_{nn}$—$CF_3$, alkoxy having 1 to 4 carbon atoms, or alkyl having 1 to 4 carbon atoms, where mm is 0 to 1, nn is 0 to 3, and ll is 0 to 4; or
(c) —$(CH_2)_{oo}$-heteroaryl which is unsubstituted or substituted by 1 to 3 radicals selected, each independently, from the group consisting of F, Cl, Br, I, —$SO_2CH_3$, —$O_{pp}$—$(CH_2)_{rr}$—$CF_3$, alkoxy having 1 to 4 carbon atoms or alkyl having 1 to 4 carbon atoms, where pp is 0 to 1, rr is 0 to 3, and oo is 0 to 4; and optionally converting the compound of Formula (I) into a pharmaceutically acceptable salt.

The invention further relates to a process for preparing an ortho-substituted pentafluorosulfanylbenzene comprising reacting a pentafluorosulfanylbenzene with a nucleophile or organometallic compound effective to ortho-substitute said pentafluorosulfanyl benzene with a substituent defined by the group R1, wherein the pentafluorosulfanyl-benzene compound has the structure of Formula (II):

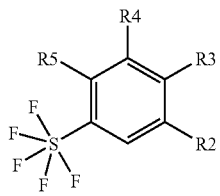

II wherein:
R2 and R4 are, each independently, hydrogen, F, Cl, Br, I, —CN, NR9R10, —OR11, —SR12, —COR13, —SO$_q$CH$_3$, —(SO$_r$)$_s$—(CH$_2$)$_t$—(CF$_2$)$_u$—CF$_3$, alkyl having 1 to 6 carbon atoms, or cycloalkyl having 3 to 8 carbon atoms, wherein 1 to 4 hydrogen atoms in said alkyl or cycloalkyl may be replaced by fluorine atoms, where q and r are, each independently, 1 to 2, s is 0 to 1, t is 0 to 1, u is 0 to 1; and where R9 and R10:
(a) are each independently, —(CH$_2$)$_v$—(CF$_2$)$_w$—CF$_3$, alkyl having 1 to 4 carbon atoms, alkylcarbonyl having 1 to 4 carbon atoms, or alkylsulfonyl having 1 to 4 carbon atoms, where v is 0 to 1 and w is 0 to 1; or
(b) together with the nitrogen atom bearing them, form a heterocycle of Formula (III):

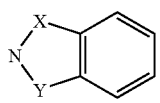

III where X and Y are, each independently, CO or SO$_2$; and where

R11 and R12 are, each independently, —(CH$_2$)$_v$—(CF$_2$)$_w$—CF$_3$, hydrogen, alkyl having 1 to 4 carbon atoms, alkylcarbonyl having 1 to 4 carbon atoms, or alkylsulfonyl having 1 to 4 carbon atoms where v is 0 to 1 and w is 0 to 1; and R13 is OH, alkyl having 1 to 6 carbon atoms or alkoxy having 1 to 6 carbon atoms;

R3 is hydrogen, F, Cl, Br, I, —CN, —NO$_2$, —COR14, —SO$_2$CH$_3$, alkyl having 1 to 6 carbon atoms, alkoxy having 1 to 4 carbon atoms, or —O$_x$—(CH$_2$)$_y$—CF$_3$, where x is 0 to 1 and y is 0 to 3; and where R14 is OH, alkyl having 1 to 6 carbon atoms, alkoxy having 1 to 6 carbon atoms or —O$_{aa}$—(CH$_2$)$_{bb}$—CF$_3$, where aa is 0 to 1 and bb is 0 to 3;

R5 is:
(a) hydrogen, F, Cl, Br, I, —CN, —SO$_2$CH$_3$, NR15R16, —O—(CH$_2$)$_{ee}$—(CF$_2$)$_{ff}$—CF$_3$, —(SO$_{gg}$)$_{hh}$—(CH$_2$)$_{jj}$—(CF$_2$)$_{kk}$—CF$_3$, alkoxy having 1 to 4 carbon atoms, alkyl having 1 to 6 carbon atoms or cycloalkyl having 3 to 8 carbon atoms, where 1 to 4 hydrogen atoms in said alkyl or cycloalkyl may be replaced by fluorine atoms, where ee and ff are, each independently, 0 to 1, gg is 0 to 2, hh is 0 to 1, jj is 0 to 4, kk is 0 to 1; and where R15 and R16 are, each independently, hydrogen, —CH$_2$—CF$_3$, alkyl having 1 to 4 carbon atoms; or
(b) —(CH$_2$)$_{ll}$-phenyl or —O-phenyl, wherein the phenyl radicals are unsubstituted or substituted by 1 to 3 radicals selected, each independently, from the group consisting of F, Cl, Br, I, —SO$_2$CH$_3$, —O$_{mm}$—(CH$_2$)$_{nn}$—CF$_3$, alkoxy having 1 to 4 carbon atoms, or alkyl having 1 to 4 carbon atoms, where mm is 0 to 1, nn is 0 to 3, and ll is 0 to 4; or
(c) —(CH$_2$)$_{oo}$-heteroaryl which is unsubstituted or substituted by 1 to 3 radicals selected, each independently, from the group consisting of F, Cl, Br, I, —SO$_2$CH$_3$, —O$_{pp}$—(CH$_2$)$_{rr}$—CF$_3$, alkoxy having 1 to 4 carbon atoms or alkyl having 1 to 4 carbon atoms, where pp is 0 to 1, rr is 0 to 3, and oo is 0 to 4.

In the preparation of the compounds of Formula (I), the procedure is to carry out an electrophilic aromatic substitution, such as a halogenation, chlorosulfonation or nitration.

In one embodiment, halogenation (R1=Cl, Br or I) is effected as described in R. C. Larock, Comprehensive Organic Transformations: A Guide to Functional Group Preparations, VCH Publishers, New York, Weinheim, 1999, pages 619-628 and in the literature cited therein. The chlorination is effected, for example, with NCIS in an inert solvent, for example isopropanol, CHCl$_3$, CH$_2$Cl$_2$ or EA at a between −30° C. and 100° C. In one embodiment, the temperature is preferably between 40° C. and the boiling point of the solvent.

In another embodiment, sulfonation or chlorosulfonation (R1=SO$_2$R6 where R6 is OH or Cl) is effected as described in March's Advanced Organic Chemistry 5th edition 2001, pages 702-703 and in the literature cited therein.

In another embodiment, nitration (R1=NO$_2$) is effected as described, for example, in Houben-Weyl, Methoden der organischen Chemie, 4th edition, Organo-Stickstoff-Verbindungen IV, part 1, Georg Thieme Verlag Stuttgart 1992, pages 262-341 and in the literature cited therein. Compounds of Formula II where R3=COOH are nitrated, for example, with a mixture of 90% HNO$_3$ and 96% H$_2$SO$_4$ at a temperature between −40° C. and 80° C., preferably between 0° C. and 40° C.

From the compounds of Formula (I) where R1=NO$_2$, it is possible to prepare the corresponding anilines (R1=NH$_2$) as described in R. C. Larock, Comprehensive Organic Transformations: A Guide to Functional Group Preparations, VCH Publishers, New York, Weinheim, 1999, 821-828 and the literature cited therein. From these anilines, it is possible to synthesize, via the diazonium salts by methods known to those skilled in the art, as described, for example, in Houben-Weyl, Methoden der organischen Chemie, 4th edition, Organo-Stickstoff-Verbindungen I, part 2, Georg Thieme Verlag Stuttgart 1990, pages 1060-1136 and in the references cited therein, the compounds of Formula (I) with further definitions of R1.

The starting compounds of Formula (II) are commercially available or can be prepared by processes similar to those described in the literature and/or known to those skilled in the art.

In the starting compounds, functional groups may also be present in protected form or in the form of precursors, and then be converted to the desired groups in the compounds of Formula I prepared by the process described above. Appropriate protecting group techniques are known to those skilled in the art.

The workup and, if desired, the purification of the products and/or intermediates is effected by conventional methods such as extraction, chromatography or crystallization and conventional dryings.

Also claimed are the compounds of Formula (I) and/or the salts thereof for use as a synthetic intermediate, in particular for use as a synthetic intermediate for preparing medicaments, diagnostic aids, liquid crystals, polymers, pesticides, herbicides, fungicides, nematicides, parasiticides, insecticides, acaricides and arthropodicides.

Examples of the various possible uses of pentafluorosulfanyl derivatives are described in the following publications: WO 9421606, WO 03093228 (insectides, acaricides); DE 19711953, GB 2276379 (herbicides); DE 10124480, DE 10353658, Angew. Chem. 1999, 111, 2174, Angew. Chem. 2000, 112, 4384 (liquid crystals); WO 03097591, DE 10353202 (medicaments, diagnostic aids); U.S. Pat. No. 5,220,070, U.S. Pat. No. 5,302,692 (polymers); WO 03093228, WO 9625401 (pesticides); GB 2276381, GB 2276380 (fungicides), U.S. Pat. No. 5,637,607 (nematicides), WO 9947139 (parasiticides), U.S. Pat. No. 6,531,501, WO 9516676 (arthropodicides).

The compounds of Formula (I) can be isolated in the form of their salts. These are obtained by the conventional methods by reaction with acids or bases. Useful acid addition salts are, for example, halides (such as hydrochlorides, or hydrobromides), lactates, sulfates, citrates, tartrates, acetates, phosphates, methylsulfonates, benzenesulfonates, p-toluenesulfonates, adipates, fumarates, gluconates, glutamates, glycerolphosphates, maleates, benzoates, oxalates and pamoates and trifluoroacetates, and in the case of the preparation of active ingredients preferably pharmaceutically acceptable salts. If the compounds contain an acidic group, they can form salts with bases, for example alkali metal salts (such as sodium or potassium salts), or ammonium salts, for example as salts with ammonia or organic amines or amino acids. They may also be in the form of a zwitterion.

List of Abbreviations

| DBU | 1,8-diazabicyclo[5.4.0]undec-7-ene |
|---|---|
| | 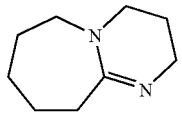 |
| DIP | diisopropyl ether |
| DIPEA | diisopropylethylamine |
| DME | 1,2-dimethoxyethane |
| DMF | N,N-dimethylformamide |
| EA | ethyl acetate (EtOAc) |
| eq. | equivalent |
| HEP | n-heptane |
| HOAc | acetic acid |
| MeOH | methanol |
| mp | melting point |
| MTB | tert-butyl methyl ether |
| NCIS | N-chlorosuccinimide |
| dppf | 1,1'bis(diphenylphosphino)ferrocene |
| RT | room temperature |
| THF | tetrahydrofuran |

EXAMPLES

Example 1

2-Methyl-5-nitro-4-pentafluorosulfuranylbenzoic acid

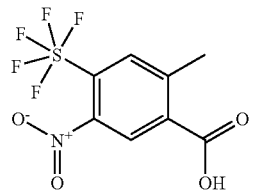

a) 4-Aminophenylsulfur pentafluoride

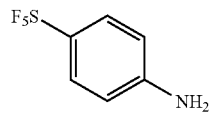

A solution of tin(II) chloride (1465 g, 7.73 mol) in concentrated (32 percent) aqueous HCl solution was heated with stirring to 80° C. and then, with ice cooling, 4-nitrophenylsulfur pentafluoride (584 g, 2.344 mol) was introduced in 8 portions within 1 h. The internal temperature was kept below 100° C. Subsequently, the mixture was stirred at an internal temperature of 85° C. for 1.5 h and then allowed to cool to 45° C. within a further hour. A mixture of ice (12 kg), NaOH (2 kg) and dichloromethane (1.5 l) was prepared and added to the reaction mixture with vigorous stirring. The phases were separated, the aqueous phase was extracted 3 times with 1 l each time of dichloromethane, and the combined organic phases were dried over $Na_2SO_4$ and concentrated under reduced pressure. 510 g of 4-aminophenylsulfur pentafluoride were obtained as a bright yellow crystalline powder, m.p. 63-65° C. (lit.: 57-59° C.)

b) 4-Amino-3-bromophenylsulfur pentafluoride

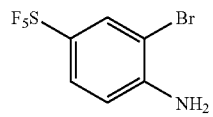

4-Aminophenylsulfur pentafluoride (510 g, 2.327 mol) was dissolved in dichloromethane (7 l), the solution was cooled to 5° C. and, while stirring, 1,3-dibromo-5,5-dimethylimidazolidine-2,4-dione (326 g, 1.14 mol) was introduced in several portions with ice cooling such that the internal temperature was kept at 3-8° C. (about 1 h). Subsequently, the mixture was stirred without external cooling for 1 h and allowed to warm to room temperature. The mixture was filtered through a bed of silica gel (volume about 1 l) and washed with dichloromethane (5.5 l), and the filtrate was concentrated under reduced pressure. About 700 g of a red-brown crystalline mass were obtained and were dissolved in n-heptane (600 ml) at 60° C. and then crystallized in a refrigerator at 4° C. Filtration with suction gave 590 g (85%) of 4-amino-3-bromophenylsulfur pentafluoride as brownish crystals, m.p. 59-59.5° C.

c) 4-Amino-3-methylphenylsulfur pentafluoride

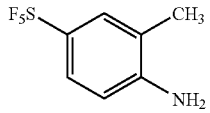

A mixture of $Cs_2CO_3$ (794 g, 2.7 mol), dimethoxyethane (2 l), water (300 ml) and trimethylboroxine (50 percent solution in THF, 225 g, 0.9 mol) was heated to 70° C., $PdCl_2$(dppf).$CH_2Cl_2$ (37 g, 45 mmol) was added, and a solution of 4-amino-3-bromophenyl sulfur pentafluoride (270 g, 0.9 mol) in dimethoxyethane (400 ml) was added dropwise within 2 h while the reaction mixture was heated to reflux. It was subsequently heated to reflux for a further 3 h and then cooled to room temperature, diluted with MTB (500 ml), filtered through a silica gel column (14×7 cm, 70-200 μm) and washed with MTB (2500 ml). The filtrate was concentrated under reduced pressure. 490 g of a black, semicrystalline mass were obtained and were subjected to a steam distillation. A total of 5.5 l of condensate was collected, from which the crystals of the product separated out. The condensate was extracted 3 times with MTB, and the combined organic phases were dried over $Na_2SO_4$ and concentrated under reduced pressure. 4-Amino-3-methylphenylsulfur pentafluoride (181 g, 76%) was obtained as colorless crystals, m.p. 65-66° C.

d) 4-Bromo-3-methylphenylsulfur pentafluoride

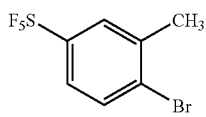

A mixture of tert-butyl nitrite (90 percent, 37 ml, 280 mmol) and $CuBr_2$ (35.8 g, 160 mmol) in acetonitrile (260 ml) was cooled to 5° C. and, while stirring and cooling with ice, a solution of 4-amino-3-methylphenylsulfur pentafluoride (30.9 g, 132.5 mmol) in MTB (140 ml) was added dropwise at 5-8° C. within 1 h. Evolution of nitrogen started after about 2 min. The mixture was then allowed to warm with stirring to room temperature within 1 h, a mixture of ice (250 g), 26 percent aqueous $NH_3$ solution (50 ml) and MTB (250 ml) was added, and the mixture was stirred for 10 min. The phases were separated, the aqueous phase was extracted 3 times with MTB (150 ml each time), and the combined organic phases were shaken once with 400 ml of water. Drying with $Na_2SO_4$ and evaporation of the organic phase gave 39 g of 4-bromo-3-methylphenylsulfur pentafluoride as a red-brown oil which was contaminated with 8 mol % 4,5-dibromo-3-methylphenylsulfur pentafluoride, but was used further without further purification. Yield 89% based on a purity of 90%.

e) 4-Cyano-3-methylphenylsulfur pentafluoride

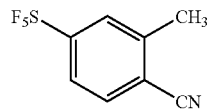

A mixture of 4-bromo-3-methylphenylsulfur pentafluoride (136.4 g, purity 80%, 0.367 mol), $Zn(CN)_2$ (72.8 g, 0.62 mol) and Zn dust (7.2 g, 0.11 mol) in dimethylacetamide (900 ml) and water (40 ml) was initially charged with nitrogen sparging, heated to 125° C. with stirring, and $PdCl_2$(dppf).$CH_2Cl_2$ (32.7 g, 40 mmol) was added. After stirring at 125° C. for one hour, $PdCl_2$(dppf).$CH_2Cl_2$ (16.3 g, 20 mmol) and Zn dust (3.6 g, 55 mmol) was again added, and stirring was continued at 125° C. for 2 h. Subsequently, the mixture was cooled to room temperature, diluted with n-heptane (400 ml) and stirred vigorously with addition of 5 N aqueous $NH_4Cl$ solution (250 ml) and water (450 ml) for 15 min. The mixture was filtered with suction through a layer of kieselguhr, the phases were separated, and the aqueous phase was extracted twice with n-heptane (200 ml). The combined organic phases were shaken with water (450 ml), dried over $MgSO_4$ and concentrated under reduced pressure. The resulting black residue was dissolved in 200 ml of n-heptane, filtered and again concentrated under reduced pressure. 78 g of a dark brown liquid were obtained and were purified by chromatography on a silica gel column (7×55 cm, 60-200 μm, 4:1 to 3:2 n-heptane/dichloromethane). The first fraction obtained was 6.5 g of 4-bromo-3-methylphenylsulfur pentafluoride (reactant) as yellowish liquid, and then 71.1 g (80%) of 4-cyano-3-methylphenylsulfur pentafluoride as a pale yellow oil.

f) 2-Methyl-4-pentafluorosulfuranylbenzoic acid

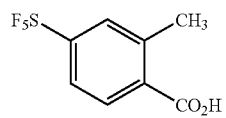

A mixture of 4-cyano-3-methylphenylsulfur pentafluoride (41.2 g, 169.4 g), NaOH (20.4 g, 510 mmol) and water (60 ml) in ethylene glycol (160 ml) was heated to 130° C. and stirred at this temperature for 4 h. It was then cooled to room temperature and diluted with MTB (150 ml) and water (250 ml), and the mixture was filtered with suction. The phases of the filtrate were separated, and the aqueous phase was acidified with concentrated aqueous HCl solution, and the precipitated solid was filtered off with suction. 41.1 g (93%) of 2-methyl-4-pentafluorosulfuranylbenzoic acid were obtained as colorless crystals, m.p. 138-139° C.

g) 2-Methyl-5-nitro-4-pentafluorosulfuranylbenzoic acid 6.0 g of 2-methyl-4-pentafluorosulfuranylbenzoic acid were dissolved in 60 ml of a 90% aqueous $HNO_3$ solution and, at RT, 6 ml of a 96% $H_2SO_4$ were added dropwise. The mixture was left to stand at RT for 28 h, then poured onto 300 g of ice, 300 ml of water were added, the mixture was stirred for 1 h and then the product was filtered off. The pale yellow solid was dried in air to give 6.5 g, m.p. 218-220° C.

Rf (DIP/2% HOAc)=0.27 MS (ES⁻): 306

Example 2

Methyl 3-amino-4-chloro-5-pentafluorosulfanylbenzoate

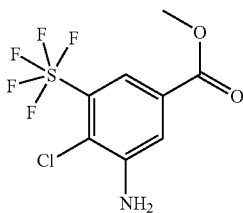

and methyl 5-amino-2-chloro-3-pentafluorosulfanylbenzoate

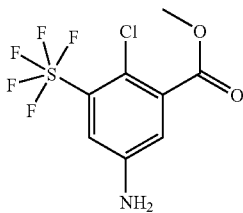

a) 3-Pentafluorosulfanylbenzoic acid

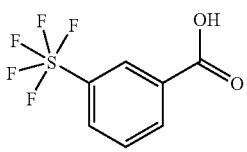

13.00 g of (3-iodophenyl)sulfur pentafluoride (Tetrahedron 56, (2000) 3399) and 6.15 g of methyl iodide were dissolved in 200 ml of diethyl ether (anhydrous) and the solution was added dropwise to 2.87 g of magnesium/20 ml of diethyl ether. The reaction mixture was stirred at reflux for one hour, then cooled to −10° C. and sparged under atmospheric pressure with $CO_2$. The mixture was stirred at RT for 16 hours, then the reaction mixture was adjusted to pH 3-4 using dilute aqueous HCl solution and extracted 3 times with 200 ml each time of EA. Drying was effected over $MgSO_4$ and the solvent was removed under reduced pressure. 7.20 g of a colorless, amorphous powder were obtained.

Rf (DIP)/2% HOAc)=0.51 MS (DCI): 249 b) 3-Nitro-5-pentafluorosulfanylbenzoic acid

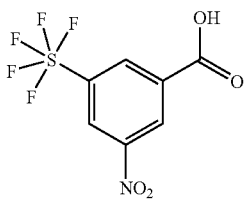

4.0 g of 3-pentafluorosulfanylbenzoic acid were dissolved at RT in 50 ml of 100% $HNO_3$ and 10 ml of $H_2SO_4$ were added with ice cooling. The mixture was stirred at RT for 6 days, then poured onto 200 g of ice and stirred for a further hour, and finally the product was filtered off with suction. 4.4 g of bright yellow crystals were obtained, m.p. 140° C.

MS (ES$^-$): 292 c) Methyl 3-nitro-5-pentafluorosulfanylbenzoate

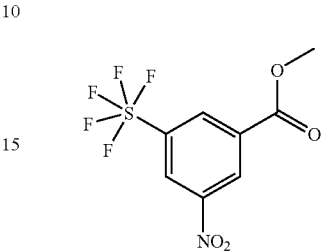

4.4 g of 3-nitro-5-pentafluorosulfanylbenzoic acid were dissolved in 100 ml of MeOH and 5.4 ml of $SOCl_2$ were added dropwise at RT. The mixture was boiled to reflux for 5 h, the volatile constituents were removed under reduced pressure and the residue was coevaporated once with 100 ml of toluene. The residue was chromatographed on silica gel using 1:8 EA/HEP and 4.2 g of a colorless oil were obtained.

Rf (EA/HEP 1:8)=0.18 MS (DCI): 308 d) Methyl 3-amino-5-pentafluorosulfanylbenzoate

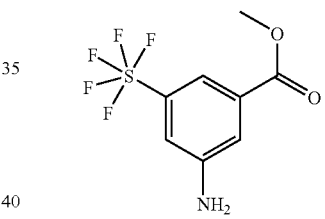

3.0 g of methyl 3-nitro-5-pentafluorosulfanylbenzoate were dissolved in 50 ml of MeOH and 5 ml of HOAc and 200 mg of Pd/C (10%) were added. The mixture was hydrogenated under a standard pressure of hydrogen atmosphere for 20 h, then hydrogenation was effected under 6 bar of hydrogen for a further 2 days. The catalyst was filtered off and the solvent removed under reduced pressure to obtain 2.5 g of an amorphous solid.

Rf (DIP)=0.48 MS (DCI): 278 e) Methyl 3-amino-4-chloro-5-pentafluorosulfanylbenzoate and methyl 5-amino-2-chloro-3-pentafluorosulfanylbenzoate 2.2 g of methyl 3-amino-5-pentafluorosulfanylbenzoate were dissolved in 20 ml of isopropanol and 1.1 g of NCIS were added at 60° C. The solution was boiled to reflux for 2 h, then allowed to cool to RT. 10 ml of a saturated aqueous $Na_2SO_3$ solution and 100 ml of a saturated aqueous $Na_2CO_3$ solution were then added and extraction was effected 3 times with 150 ml each time of EA. Drying was effected over $MgSO_4$, the solvent was removed under reduced pressure and the residue was chromatographed on silica gel using 1:6 EA/HEP. 508 mg of methyl 3-amino-4-chloro-5-pentafluorosulfanylbenzoate and 94 mg of methyl 5-amino-2-chloro-3-pentafluorosulfanylbenzoate as well as 1.39 g of methyl 3-amino-2-chloro-5-pentafluorosulfanylbenzoate were obtained; each as colorless oils.

Rf (EA/HEP 1:6)=0.26: methyl 3-amino-2-chloro-5-pentafluorosulfanylbenzoate Rf (EA/HEP 1:6)=0.15: methyl 3-amino-4-chloro-5-pentafluorosulfanylbenzoate Rf (EA/HEP 1:6)=0.26: methyl 5-amino-2-chloro-5-pentafluorosulfanylbenzoate MS (ES+): each 352 (M+CH$_3$C≡N)

Example 3

2-Chloro-3-pentafluorosulfanylaniline and 4-chloro-3-pentafluorosulfanylaniline

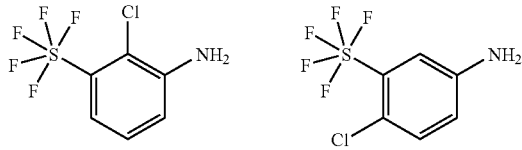

8.00 g of 3-pentafluorosulfanylaniline (Tetrahedron 56, (2000) 3399) were dissolved in 200 ml of isopropanol and 4.87 g of NCIS were added in portions at 60° C. (within 30 minutes). The mixture was stirred at 60° C. for a further 20 minutes, then boiled under reflux for 2 h. The reaction mixture was allowed to cool to RT and half of the solvent was removed under reduced pressure. 300 ml of a semisaturated aqueous NaHCO$_3$ solution and 50 ml of a saturated aqueous Na$_2$SO$_3$ solution were then added and extraction was effected 3 times with 100 ml each time of CH$_2$Cl$_2$. Drying was effected over MgSO$_4$, the solvent was removed under reduced pressure and the residue was chromatographed on silica gel using 1:4 EA/HEP. 2.02 g of 2-chloro-3-pentafluorosulfanylaniline and 1.10 g of 4-chloro-3-pentafluorosulfanylaniline as well as 2.73 g of 2-chloro-5-pentafluorosulfanylaniline were obtained.

Rf (EA/HEP 1:4)=0.31: 2-chloro-5-pentafluorosulfanylaniline Rf (EA/HEP 1:4)=0.18: 2-chloro-3-pentafluorosulfanylaniline Rf (EA/HEP 1:4)=0.11: 4-chloro-3-pentafluorosulfanylaniline MS (DCI): each 253

Example 4

2-(4-Nitro-3-pentafluorosulfanylphenyl)isoindole-1,3-dione and 2-(2-nitro-5-pentafluorosulfanylphenyl)isoindole-1,3-dione

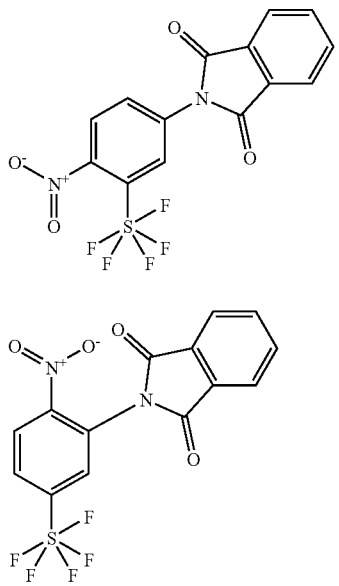

a) 2-(3-Pentafluorosulfanylphenyl)isoindole-1,3-dione:

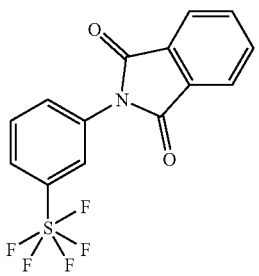

15 g (68.44 mmol) of 3-pentafluorosulfanylphenylamine was suspended with 10.14 g (68.44 mmol) of phthalic anhydride in 40 ml of a acetic acid and boiled under reflux for 2 h. The cool reaction mixture was admixed with 400 ml of water, heated in an ultrasound bath for 30 min and filtered. The residue was washed with water and subsequently with a little ethanol and dried under reduced pressure. 2-(3-Pentafluorosulfanylphenyl)isoindole-1,3-dione was obtained with a melting point of 188-190° C.

b) 2-(4-Nitro-3-pentafluorosulfanylphenyl)isoindole-1,3-dione and 2-(2-nitro-5-pentafluorosulfanylphenyl)isoindole-1,3-dione 1 g (2.863 mmol) of 2-(3-pentafluorosulfanylphenyl)isoindole-1,3-dione was dissolved at 0° C. in 3.29 ml of concentrated nitric acid, and the mixture was stirred at 0° C. for 2 h. Afterward, the mixture was left to stand at room temperature overnight. The reaction solution was added to 50 g of ice-water and the mixture was stirred for 1 h; then the precipitate was filtered off with suction, washed with water, dried and purified chromatographically on silica gel using toluene as the eluent. 2-(4-Nitro-3-pentafluorosulfanylphenyl)isoindole-1,3-dione having a melting point of 200-203° C. and 2-(2-nitro-5-pentafluorosulfanylphenyl)isoindole-1,3-dione having a melting point of 175-177° C. were obtained in a ratio of 1:2.

Example 5

2-(4-Amino-3-pentafluorosulfanylphenyl)isoindole-1,3-dione

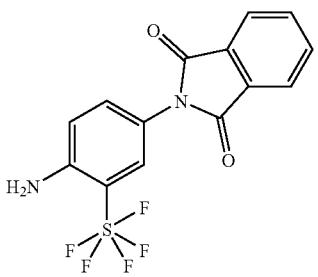

1.94 g (4.92 mmol) of 2-(4-nitro-3-pentafluorosulfanylphenyl)isoindole-1,3-dione (prepared in example 4) were dissolved in 20 ml of methanol, admixed with 10% palladium on activated carbon and hydrogenated at room temperature at a hydrogen pressure of 5 bar. On completion of reaction, the catalyst was filtered off and the filtrate concentrated. The residue was stirred in a mixture of dichlo-

21 romethane and n-heptane, filtered with suction and dried under reduced pressure. 2-(4-amino-3-pentafluorosulfanylphenyl)isoindole-1,3-dione having a melting point of 176-178° C. was obtained.

When the above-described reaction was terminated prematurely, 2-(4-hydroxyamino-3-pentafluorosulfanylphenyl)isoindole-1,3-dione

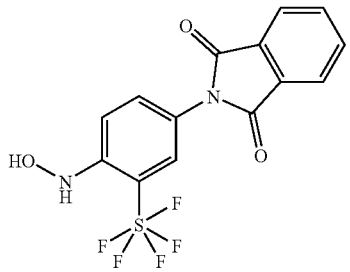

having a melting point (with decomposition) of 171-173° C. was obtained.

Example 6

4-(1,3-Dioxo-1,3-dihydroisoindole-2-yl)-2-pentafluorosulfanylbenzonitrile

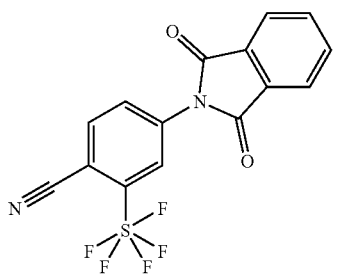

0.46 ml (8.24 mmol) of semiconcentrated sulfuric acid was slowly added dropwise at 0° C. to a solution of 1 g (2.74 mmol) of 2-(4-amino-3-pentafluorosulfanylphenyl)isoindole-1,3-dione (prepared in example 5) in acetic acid. The mixture was stirred at 0° C. for 10 min; then a solution of 189.4 mg of sodium nitrite in 2 ml of water was slowly added dropwise with stirring, and the resulting solution was stirred at 0° C. for 30 min. This solution was finally added dropwise to a solution, cooled to 0° C., of 246 mg (2.74 mmol) of copper(I) cyanide and 536 mg (8.23 mmol) of potassium cyanide in 5 ml of water. The reaction mixture was stirred at 0° C. for 30 min and afterward at room temperature for another 3 h. After the end of the reaction, the mixture was added to water and the aqueous phase extracted twice with ethyl acetate. The organic phase was dried over magnesium sulfate and filtered, the filtrate was concentrated and the residue purified chromatographically on silica gel first with toluene and then with 20/1 toluene/ethyl acetate. 4-(1,3-Dioxo-1,3-dihydroisoindol-2-yl)-2-pentafluorosulfanylbenzonitrile was obtained. $^{1}$H NMR (500 MHz; d$_6$-dmso: δ [ppm]=8.4 (m, 2H); 8.1-7.95 (m, 5H).

22

Example 7

4-Amino-2-pentafluorosulfanylbenzonitrile and ethyl N-(4-cyano-3-pentafluorosulfanylphenyl)phthalamate

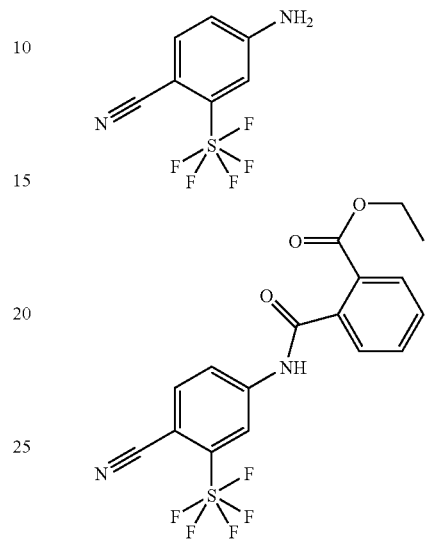

610 mg (1.63 mmol) of 4-(1,3-dioxo-1,3-dihydroisoindol-2-yl)-2-pentafluorosulfanylbenzonitrile (prepared in example 6) were dissolved in 30 ml of ethanol and admixed with 100 mg (1.956 mmol) of hydrazine hydrate (100%). The mixture was stirred at room temperature overnight. Afterward, the reaction mixture was concentrated under reduced pressure and the residue was purified by chromatography (preparative HPLC; Purospher STAR RP-18e (10 μm); eluent: 5/95→95/5 [45 min.] acetonitrile/water (0.5% trifluoroacetic acid)). 4-Amino-2-pentafluorosulfanylbenzonitrile ($^{1}$H NMR (500 MHz; d$_6$-dmso) δ [ppm]=7.65 (s, 1H); 7.2 (s, 1H, 6.8 (m, 3H)) and N-(4-cyano-3-pentafluorosulfanylphenyl)phthalamate ($^{1}$H NMR (500 MHz; d$_6$-dmso) δ [ppm]=11.3 (s, 1H); 8.6 (s, 1H); 8.2 (d, 1H); 8.1 (d, 1H); 7.95 (d, 1H); 7.75 (m, 1H); 7.7 (m, 2H); 4.2 (q, 2H); 1.15 (t, 3H)) were obtained.

Example 8

N-(4-Nitro-3-pentafluorosulfanylphenyl)acetamide and N-(2,4-dinitro-5-pentafluorosulfanylphenyl)acetamide

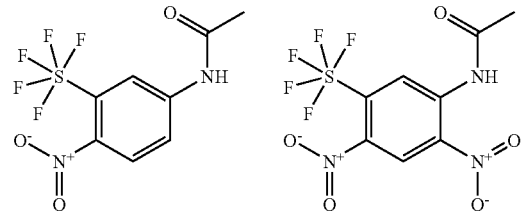

1.0 g of N-(3-pentafluorosulfanylphenyl)acetamide (preparation as in Tetrahedron 56, (2000) 3399) was dissolved in portions at 0-3° C. in 10 ml of 90% HNO$_3$. The mixture was stirred at 0° C. for 15 minutes, then poured onto 100 g of ice and extracted 3 times with 100 ml each time of EA. Drying was effected over MgSO$_4$, the solvent was removed under reduced pressure and the residue was chromatographed on silica gel using DIP. 195 mg of N-(4-nitro-3-pentafluorosulfanylphenyl)acetamide and 280 mg of N-(2,4-dinitro-5-pentafluorosulfanylphenyl)acetamide as well as 645 mg of N-(2-nitro-5-pentafluorosulfanylphenyl)acetamide were obtained.

Rf (DIP)=0.41: N-(2-nitro-5-pentafluorosulfanylphenyl)acetamide MS (EI): 306 Rf (DIP)=0.18: N-(2,4-dinitro-5-pentafluorosulfanylphenyl)acetamide MS (EI): 351 Rf (DIP)= 0.11: N-(4-nitro-3-pentafluorosulfanylphenyl)acetamide MS (EI): 306

Example 9

N-(4-Nitro-3-pentafluorosulfanylphenyl)acetamide

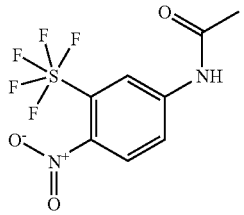

20.00 g of N-(3-pentafluorosulfanylphenyl)acetamide (preparation as in Tetrahedron 56, (2000) 3399) were dissolved in portions at from −35° C. to −40° C. in 100 ml of 90% HNO$_3$. The mixture was stirred at −40° C. for 15 minutes, then poured onto 1 kg of ice and stirred at RT for 1 h. The product was then filtered, washed with water and dried under reduced pressure. Chromatography on silica gel using DIP afforded 3.61 g of N-(4-nitro-3-pentafluorosulfanylphenyl)acetamide as well as 17.00 g of N-(2-nitro-5-pentafluorosulfanylphenyl)acetamide.

Rf (DIP)=0.41: N-(2-nitro-5-pentafluorosulfanylphenyl)acetamide MS (EI): 306 Rf (DIP)=0.11: N-(4-nitro-3-pentafluorosulfanylphenyl)acetamide MS (EI): 306

Example 10

1,3-Dibromo-2-methoxy-4-nitro-5-pentafluorosulfanylbenzene

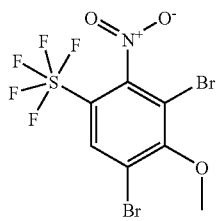

a) 4-Pentafluorosulfanylphenol

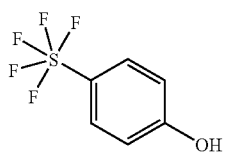

40.00 g of 4-pentafluorosulfanylaniline were suspended in 500 ml of a 35% aqueous H$_2$SO$_4$ solution and a solution of 13.85 g of NaNO$_2$ in 30 ml of water was added dropwise at 0° C. over a period of 10 minutes. Subsequently, the mixture was stirred at 0° C. for 35 minutes, then a solution, at 0° C., of 171.10 g of Cu(NO$_3$)$_2$ in 200 ml of water was poured in and, directly thereafter, 26.11 g of Cu$_2$O were added in portions. The mixture is stirred at RT for a further 2 hours, then extraction is effected 3 times with 200 ml each time of CH$_2$Cl$_2$. Drying was effected over MgSO$_4$ and the solvent was removed under reduced pressure. 38.00 g of a pale yellow oil were obtained which was used further without purification.

b) 4-Methoxypentafluorosulfanylbenzene

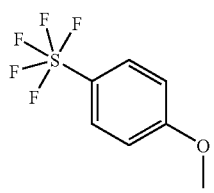

5.00 g of 4-pentafluorosulfanylphenol were dissolved in 50.00 g of dimethyl carbonate and 3.46 g of DBU were added. The mixture was boiled under reflux for 10 hours, then allowed to cool and diluted with 200 ml of EA. Subsequently, the mixture was washed twice with 100 ml each time of a 5% aqueous HCl solution, then with 100 ml of a 5% aqueous NaOH solution. Drying was effected over MgSO$_4$ and the solvent was removed under reduced pressure. Chromatography on silica gel using 1:1 DIP/HEP afforded 2.2 g of a colorless oil.

Rf (DIP/HEP 1:1)=0.52 c) 2,6-Dibromo-4-pentafluorosulfanylphenol

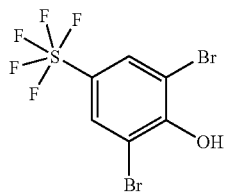

3.34 g of 4-methoxypentafluorosulfanylbenze were dissolved in 200 ml of CHCl$_3$ and 0.46 g of FeBr$_2$ were added. At RT, 6.84 g of bromine were then added dropwise and the mixture was stirred at RT for 4 days. Subsequently, a further 400 mg of FeBr$_2$ were added and the mixture was stirred at RT for a further 23 hours. The reaction mixture was then poured cautiously onto 100 ml of a saturated aqueous Na$_2$SO$_3$ solution and extracted 3 times with 50 ml each time of CH$_2$Cl$_2$. Drying was effected over MgSO$_4$ and the solvent was removed under reduced pressure. Chromatography on silica gel using DIP afforded 3.00 g of an amorphous solid.

Rf (DIP)=0.22 d) 1,3-Dibromo-2-methoxy-5-pentafluorosulfanylbenzene

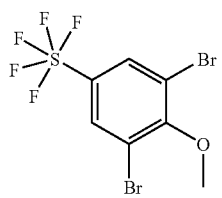

450 mg of 2,6-dibromo-4-pentafluorosulfanylphenol, 329 mg of K$_2$CO$_3$ and 186 mg of CH$_3$I were stirred at RT in 5 ml of anhydrous DMF for 24 hours. Subsequently, the reaction mixture was poured onto 100 ml of EA and extracted 3 times with 30 ml each time of water. Drying was effected over MgSO$_4$ and the solvent was removed under reduced pressure to obtain 500 mg of a colorless oil.

Rf (DIP/HEP 1:1)=0.51 MS (EI): 392 e) 1,3-Dibromo-2-methoxy-4-nitro-5-pentafluorosulfanyl-benzene 630 mg of 1,3-dibromo-2-methoxy-5-pentafluorosulfanylbenzene were stirred in 2 ml of a 90% aqueous HNO$_3$ solution at 0° C. for 1 hour. Subsequently, the mixture was stirred at RT for 20 minutes and then poured onto 50 g of ice. An aqueous Na$_2$CO$_3$ solution was used to adjust to pH=6 and extraction was effected three times with 50 ml each of EA. Drying was effected over Na$_2$SO$_4$ and the solvent was removed under reduced pressure. Chromatography on silica gel using 1:3 DIP/HEP afforded 260 mg of a pale yellow oil.

Rf (DIP/HEP 1:3)=0.40

Example 11

1-Bromo-3-chloro-2-methoxy-4-nitro-5-pentafluorosulfanylbenzene and 3-bromo-1-chloro-2-methoxy-4-nitro-5-pentafluorosulfanylbenzene

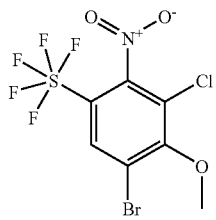 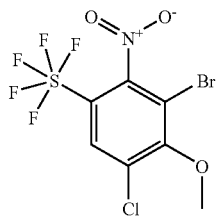

a) 2-Chloro-4-pentafluorosulfanylphenol 5.00 g of 4-pentafluorosulfanylphenol (prepared in example 11a) were dissolved in 100 ml of acetic acid and a chlorine gas stream was passed through at 0° C. for 10 minutes. This warmed the solution to 30° C. which was subsequently stirred at RT for a further 90 minutes. Argon was used to drive the chlorine out of the solution and the solvent was subsequently removed under reduced pressure. 5.50 g of a pale yellow oil were obtained.

Rf (DIP)=0.23 b) 2-Chloro-1-methoxy-4-pentafluorosulfanylbenzene

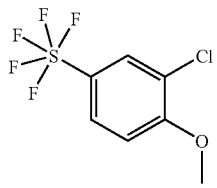

5.50 g of 2-chloro-4-pentafluorosulfanylphenol, 7.89 g of K$_2$CO$_3$ and 4.05 g of CH$_3$I were stirred at RT in 30 ml of anhydrous DMF for 2 hours and left to stand at RT for 2 days. The mixture was then diluted with 300 ml of EA and washed 3 times with 100 ml each time of water. Drying was effected with Na$_2$SO$_4$ and the solvent was removed under reduced pressure to obtain 5.40 g of a pale yellow oil.

Rf (DIP)=0.88 c) 2-Bromo-6-chloro-4-pentafluorosulfanylphenol

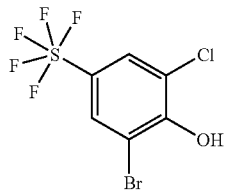

5.30 g of 2-chloro-1-methoxy-4-pentafluorosulfanylbenzene were dissolved in 150 ml of CHCl$_3$ and admixed with 4.73 g of bromine and 638 mg of FeBr$_2$. The mixture was stirred at RT for 18 hours, then admixed with a further 200 mg of FeBr$_2$, stirred at RT for 6 hours and then admixed with a further 300 mg of FeBr$_2$, stirred at RT for 2 hours and left to stand at RT for 18 hours. The reaction mixture was then poured onto 300 ml of a saturated aqueous Na$_2$SO$_3$ solution and extracted with 300 ml of CH$_2$Cl$_2$. The organic phase was then washed with 100 ml of water and dried over Na$_2$SO$_4$, and the solvent was removed under reduced pressure. 4.20 g of a colorless oil were obtained which was reacted further without purification.

d) 1-Bromo-3-chloro-2-methoxy-5-pentafluorosulfanylbenzene

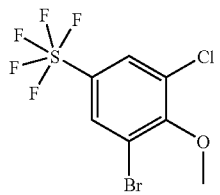

4.20 g of 2-bromo-6-chloro-4-pentafluorosulfanylphenol were stirred together with 3.48 g of K$_2$CO$_3$ and 2.68 g of CH$_3$I in 50 ml of anhydrous DMF at RT for 24 hours. The solvent was then removed under reduced pressure and subsequently taken up with 100 ml each of water and EA. The phases were left to separate and extraction was then effected twice more with 100 ml each time of EA. Drying was effected over Na$_2$SO$_4$ and the solvent was removed under reduced pressure. Chromatography on silica gel using 1:1 DIP/HEP afforded 3.44 g of a colorless viscous liquid.

Rf (DIP/HEP 1:1)=0.53 MS (EI): 346 e) 1-Bromo-3-chloro-2-methoxy-4-nitro-5-pentafluorosulfanylbenzene and 3-bromo-1-chloro-2-methoxy-4-nitro-5-pentafluorosulfanylbenzene 3.40 g of 1-bromo-3-chloro-2-methoxy-5-pentafluorosulfanylbenzene were added dropwise at from 0° C. to 5° C. to 40 ml of a 90% aqueous HNO$_3$ solution. The mixture was stirred at 0° C. for 60 minutes, then stirred at RT for 90 minutes. Subsequently, the reaction mixture was poured onto 200 g of ice and extracted 3 times with 200 ml each time of EA. Drying was effected over Na$_2$SO$_4$ and the solvent was removed under reduced pressure. Chromatography on silica gel using 1:3 DIP/HEP afforded 2.00 g of a pale yellow oil.

MS (EI): 391

Example 12

2-Chloro-4-nitro-5-pentafluorosulfanylaniline

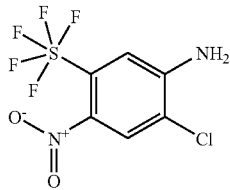

2.60 g of 2-chloro-5-pentafluorosulfanylaniline (example 3) were added dropwise at 0° C. to 30 ml of 100% HNO$_3$. The mixture was stirred at 0° C. for 1 hour, then poured onto 100 g of ice and adjusted to pH=7 using saturated aqueous NaHCO$_3$ solution. Extraction was then effected 3 times using 100 ml each time of EA, then drying was effected over MgSO$_4$. The solvent was removed under reduced pressure to obtain 2.50 g of a pale yellow oil.

Rf (EA)=0.13

What is claimed is:

1. A compound of Formula I:

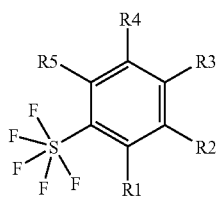

wherein:

R1 is:
- (a) Cl, Br, I, —CN, —SO$_2$R6, NO$_2$, alkoxy having 1 to 4 carbon atoms, NR7R8, —O—(CH$_2$)$_b$—(CF$_2$)$_c$—CF$_3$, —(SO$_d$)$_e$—(CH$_2$)$_f$—(CF$_2$)$_g$—CF$_3$, alkyl having 1 to 6 carbon atoms or cycloalkyl having 3 to 8 carbon atoms, wherein 1 to 4 hydrogen atoms in said cycloalkyl may be replaced by fluorine, atoms; where a, b and c are, each independently, 0 to 1, d is 0 to 2, e is 0 to 1, f is 0 to 4 and g is 0 to 1; and where R6 is OH, F, Cl, Br, I or alkyl having 1 to 4 carbon atoms; and R7 and R8 are, each independently, —CH$_2$—CF$_3$, hydrogen, or alkyl having 1 to 4 carbon atoms; or
- (b) —CH$_2$)$_h$-phenyl or —O-phenyl, wherein the phenyl radicals are unsubstituted or substituted by 1 to 3 radicals selected, each independently, from the group consisting of F, Cl, Br, I, —O$_j$—(CH$_2$)$_k$—CF$_3$, —SO$_2$CH$_3$, alkoxy having 1 to 4 carbon atoms, and alkyl having 1 to 4 carbon atoms, where j is 0 to 1, k is 0 to 3, and h is 0 to 4; or
- (c) —(CH$_2$)$_l$-heteroaryl which is unsubstituted or substituted by 1 to 3 radicals selected, each independently, from the group consisting of F, Cl, Br, I, —O$_m$—(CH$_2$)$_n$—CF$_3$, —SO$_2$CH$_3$ alkoxy having 1, to 4 carbon atoms, and alkyl having 1 to 4 carbon atoms, where m is 0 to 1, n is 0 to 3, and l is 0 to 4;

R2 and R4 are, each independently, hydrogen, F, Cl, Br, I, —CN, NR9R10, —OR11, —SR12, —COR13, —SO$_q$CH$_3$, —(SO$_r$)$_s$—(CH$_2$)$_t$—(CF$_2$)$_u$—CF$_3$, alkyl having 1 to 6 carbon atoms, or cycloalkyl having 3 to 8 carbon atoms in said alkyl or cycloalkyl may be replaced by fluorine atoms, where q and r are, each independently, 1 to 2, s is 0 to 1, t is 0 to 4, u is 0 to 1; and where R9 and R10:
- (a) are each independently, —(CH$_2$)$_v$—(CF$_2$)$_w$—CF$_3$, alkyl having 1 to 4 carbon atoms, alkylcarbonyl having 1to 4 carbon atoms, or alkylsulfonyl having 1 to 4 carbon atoms, where v is 0 to 4 and w is 0 to 1; or
- (b) together with the nitrogen atom bearing them, form a heterocycle of Formula (III):

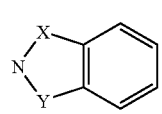

where X and Y are, each independently, CO or SO$_2$; and where R11 and R12 are each independently, —(CH$_2$)$_v$—(CF$_2$)$_w$—CF$_3$, hydrogen, alkyl having 1 to 4 carbon atoms, alkylcarbonyl having 1to 4 carbon atoms, or alkylsulfonyl having 1 to 4 carbon atoms where v is 0 to 4 and w is 0 to 1; and R13 is OH, alkyl having 1 to 6 carbon atoms or alkoxy having 1to 6 carbon atoms;

R3 is hydrogen, F, Cl, Br, I, CN, —NO$_2$, —COR14, —SO$_2$CH$_3$, alkyl having 1 to 6 carbon atoms, alkoxy having 1to 4 carbon atoms, or —O$_x$—(CH$_2$)$_y$—CF$_3$, where x is 0 to 1 and y is 0 to 3; and where R14 is OH, alkyl having 1 to 6 carbon atoms, alkoxy having 1 to 6 carbon atoms or —O$_{aa}$—(CH$_2$)$_{bb}$—CF$_3$, where aa is 0 to 1 and bb is 0 to 3;

R5 is:
- (a) hydrogen, F, Cl, Br, I, —CN, —SO$_2$CH$_3$, NR15R16, —O—(CH$_2$)$_{ee}$—(CF$_2$)$_{ff}$—CF$_3$, —(SO$_{gg}$)$_{hh}$—(CH$_2$)$_{jj}$—(CF$_2$)$_{kk}$—CF$_3$, alkoxy having 1to 4 carbon atoms, alkyl having 1 to 6 carbon atoms or cycloalkyl having 3 to 8 carbon atoms, where 1 to 4 hydrogen atoms in said alkyl or cycloalkyl may be replaced by fluorine atoms, where ee and ff are, each independently, 0 to 1, gg is 0 to 2, hh is 0 to 1, jj is 0 to 4, kk is 0 to 1; and where R15 and R16 are, each independently, hydrogen, —CH$_2$—CF$_3$, alkyl having 1 to 4 carbon atoms; or
- (b) —(CH$_2$)$_{ll}$-phenyl or —O-phenyl wherein the phenyl radicals are unsubstituted or substituted by 1 to 3 radicals selected, each independently, from the group consisting of F, Cl, Br, I, —SO$_2$CH$_3$, —O$_{mm}$—(CH$_2$)$_{nn}$—CF$_3$, alkoxy having 1 to 4 carbon atoms, or alkyl having 1to 4 carbon atoms, where mm is 0 to 1, nn is 0 to 3, and ll is 0 to 4; or
- (c) —(CH$_2$)$_{oo}$-heteroaryl which is unsubstituted or substituted by 1 to 3 radicals selected, each independently, from the group consisting of F, Cl, Br, I, —SO$_2$CH$_3$, —O$_{pp}$—(CH$_2$)$_{rr}$—CF$_3$, alkoxy having 1 to 4 carbon atoms or alkyl having 1 to 4 carbon atoms, where pp is 0 to 1, rr is 0 to 3, and oo is 0 to 4;

or a salt of a compound of Formula (I), excluding compounds of Formula (I) and the corresponding salts wherein, in the same molecule:

R2 and R4 are each Cl and R3 is F or Cl;

R2 and R4 are either Cl or CN, wherein R2 and R4 have a total of one Cl and one CN substituent, and R3 is Cl; or R1 is NO$_2$ and the other substituents are each hydrogen.

2. The compound of claim 1, wherein:

R1 is:
(a) Cl, Br, I, —CN, —SO$_2$R6, NO$_2$ alkoxy having 1to 4 carbon atoms, NR7R8, —O—(CH$_2$)$_b$—(CF$_2$)$_c$—CF$_3$, —(SO$_d$)$_e$—(CH$_2$)$_f$—(CF$_2$)$_g$—CF$_3$, alkyl having 1 to 6 carbon atoms or cycloalkyl having 3 to 8 carbon atoms, wherein 1 to 4 hydrogen atoms in said alkyl or cycloalkyl may be replaced by fluorine atoms; where a, b and c are, each independently, 0 to 1, d is 0 to 2, e is 0 to 1, f is 0 to 4, and g is 0 to 1; and where R6 is OH, F, Cl, Br, I or alkyl having 1 to 4 carbon atoms; and R7 and R8 are, each independently, —CH$_2$—CF$_3$, hydrogen, or alkyl having 1 to 4 carbon atoms; or
(b) —(CH$_2$)$_h$-phenyl or —O-phenyl, wherein the phenyl radicals are unsubstituted or substituted by 1 to 3 radicals selected, each independently, from the group consisting of F, Cl, Br, I, —O$_j$—(CH$_2$)$_k$—CF$_3$, —SO$_2$CH$_3$, alkyl having 1 to 4 carbon atoms, and alkyl having 1 to 4 carbon atoms, where j is 0 to 1, k is 0 to 3, and h is 0 to 4; or
(c) —(CH$_2$)$_l$-heteroaryl which is unsubstituted or substituted by 1 to 3 radicals selected, each independently, from the group consisting of F, Cl, Br, I, —O$_m$—(CH$_2$)$_n$—CF$_3$, —SO$_2$CH$_3$, alkoxy having 1 to 4 carbon atoms, and alkyl having 1 to 4 carbon atoms, where m is 0 to 1, n is 0 to 3, and l is 0 to 4;

R2 and R4 are, each independently, hydrogen, F, Cl, Br, I, —CN, NR9R10, —OR11, —SR12, —COR13, —(SO$_r$)$_s$—(CH$_2$)$_t$—(CF$_2$)$_u$—CF$_3$, alkyl having 1 to 6 carbon atoms, or cycloalkyl having 3 to 8 carbon atoms, wherein 1 to 4 hydrogen atoms in said alkyl or cycloalkyl may be replaced by fluorine atoms, where r is 1 to 2, s is 0 to 1, t is 0 or 1, u is 0 or 1; and where R9 and R10:
(a) are each independently, —(CH$_2$)$_v$—(CF$_2$)$_w$—CF$_3$, alkyl having 1 to 4 carbon atoms, alkylcarbonyl having 1 to 4 carbon atoms, or alkylsulfonyl having 1 to 4 carbon atoms, where v is 0 or 1 and w is 0 to 1; or
(b) together with the nitrogen atom bearing them, form a heterocycle of Formula (III):

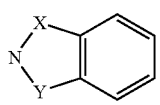

III where X and Y are, each independently, CO or SO$_2$; and where

R11 and R12 are, each independently, —(CH$_2$)$_v$—(CF$_2$)$_w$—CF$_3$, hydrogen, alkyl having 1 to 4 carbon atoms, alkylcarbonyl having 1 to 4 carbon atoms, or alkylsulfonyl having 1 to 4 carbon atoms where v is 0 or 1 and w is 0 or 1; and R13 is OH, alkyl having 1 to 6 carbon atoms or alkoxy having 1 to 6 carbon atoms;

R3 is hydrogen, F, Cl, Br, I, —CN, —NO$_2$, —COR14, —SO$_2$CH$_3$, alkyl having 1 to 6 carbon atoms, alkoxy having 1 to 4 carbon atoms, or —O$_x$—(CH$_2$)$_y$—CF$_3$, where x is 0 to 1 and y is 0 to 3; and where R14 is OH, alkyl having 1 to 6 carbon atoms, alkoxy having 1 to 6 carbon atoms or —O$_{aa}$—(CH$_2$)$_{bb}$—CF$_3$, where aa is 0 to 1 and bb is 0 to 3;

R5 is:
a) hydrogen, F, Cl, Br, I, —CN, —SO$_2$CH$_3$, NR15R16, —O—(CH$_2$)$_{ee}$—(CF$_2$)$_{ff}$—CF$_3$, —(SO$_{gg}$)$_{hh}$—(CH$_2$)$_{jj}$—(CF$_2$)$_{kk}$—CF$_3$, alkoxy having 1 to 4 carbon atoms, alkyl having 1 to 6 carbon atoms or eye cycloalkyl having 3 to 8 carbon atoms, where 1 to 4 hydrogen atoms in said alkyl or cycloalkyl may be replaced by fluorine atoms, where ee and ff are, each independently. 0 to 1, gg is 0 to 2, hh is 0 to 1, jj is 0 to 4, kk is 0 to 1;

and where

R15 and R16 are, each independently, hydrogen, —CH$_2$—CF$_3$, alkyl having 1 to 4 carbon atoms; or
(b) —(CH$_2$)$_{ll}$-phenyl or —O-phenyl, wherein the phenyl radicals are unsubstituted or substituted by 1 to 3 radicals selected, each independently, from the group consisting of F, Cl, Br, I, —SO$_2$CH$_3$, —O$_{mm}$—(CH$_2$)$_{nn}$—CF$_3$, alkoxy having 1 to 4 carbon atoms, or alkyl having 1 to 4 carbon atoms, where mm is 0 to 1, nn is 0 to 3, and ll is 0 to 4; or
(c) —(CH$_2$)$_o$o-heteroaryl which is unsubstituted or substituted by 1 to 3 radicals selected, each independently, from the group consisting of F, Cl, Br, I, —SO$_2$CH$_3$, —O$_{pp}$—(CH$_2$)$_{rr}$—CF$_3$, alkoxy having 1 to 4 carbon atoms or alkyl having 1 to 4 carbon atoms, where pp is 0 to 1, rr is 0 to 3, and oo is 0 to 4;

or a salt of a compound of Formula (I), excluding compounds of Formula (I) and the corresponding salts wherein, in the same molecule:

R2 and R4 are each Cl and R3 is F or Cl;

R2 and R4 are either Cl or CN, wherein R2 and R4 have a total of one Cl and one CN substituent, and R3 is Cl; or R1 is NO$_2$ and the other substituents are each hydrogen.

3. The compound of claim 1, wherein:

R1 is Cl, Br, I, —SO$_2$R6 or NO$_2$; and where

R6 is OH, F, Cl, Br, I or alkyl having 1 to 4 carbon atoms;

R2 and R4 are, each independently, hydrogen, F, Cl, Br, I, —CN, NR9R10, —OR11, —SR12, —COR13, —(SO$_r$)$_s$—(CH$_2$)$_t$—(CF$_2$)$_u$—CF$_3$, alkyl having 1 to 6 carbon atoms, or cycloalkyl having 3 to 8 carbon atoms, wherein 1 to 4 hydrogen atoms in said alkyl or cycloalkyl may be replaced by fluorine atoms, where r is 1 to 2, s is 0 to 1, t is 0 or 1, u is 0 or 1; and where R9 and R10:
(a) are each independently, —(CH$_2$)$_v$—(CF$_2$)$_w$—CF$_3$, alkyl having 1 to 4 carbon atoms, alkylcarbonyl having 1 to 4 carbon atoms, or alkylsulfonyl having 1 to 4 carbon atoms, where v is 0 or 1 and w is 0 or 1; or
(b) together with the nitrogen atom bearing them, form a heterocyclo of Formula (IIIa):

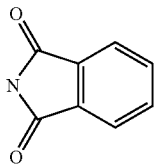

IIIa

R11 and R12 are, each independently, —(CH$_2$)$_v$—(CF$_2$)$_w$—CF$_3$, hydrogen, alkyl having 1 to 4 carbon atoms, alkylcarbonyl having 1 to 4 carbon atoms, or alkylsulfonyl having 1 to 4 carbon atoms where v is 0 or 1 and w is 0 or 1; and R13 is OH, alkyl having 1 to 6 carbon atoms or alkoxy having 1 to 6 carbon atoms;

R3 is hydrogen, F, Cl, Br, I, —CN, —NO$_2$, —COR14, —SO$_2$CH$_3$, alkyl having 1 to 6 carbon atoms, alkoxy having 1 to 4 carbon atoms, or —O$_x$—(CH$_2$)$_y$—CF$_3$, where x is 0 or 1 and y is 0 to 3; and where R14 is OH, alkyl having 1 to 6 carbon atoms, alkoxy having 1 to 6 carbon atoms or —O$_{aa}$—(CH$_2$)$_{bb}$—CF$_3$, where aa is 0 to 1 and bb is 0 to 3;

R5 is:
(a) hydrogen, F, Cl, Br, I, —CN, —SO$_2$CH$_3$, NR15R16, —O—(CH$_2$)$_{ee}$—(CF$_2$)$_{ff}$—CF$_3$, —(SO$_{gg}$)$_{hh}$—(CH$_2$)$_{jj}$—(CF$_2$)$_{kk}$—CF$_3$, alkoxy having 1 to 4 carbon atoms, alkyl having 1 to 6 carbon atoms or cycloalkyl having 3 to 8 carbon atoms, where 1 to 4 hydrogen atoms in said alkyl or cycloalkyl may be replaced by fluorine atoms, where ee and ff are, each independently, 0 to 1, gg is 0 to 2, hh is 0 to 1, jj is 0 to 4, kk is 0 to 1; and where R15 and R16 are, each independently, hydrogen, —CH$_2$—CF$_3$, alkyl having 1 to 4 carbon atoms; or (b) —(CH$_2$)$_{ll}$-phenyl or —O-phenyl, wherein the phenyl radicals are unsubstituted or substituted by 1 to 3 radicals selected, each independently, from the group consisting of F, Cl, Br, I, —SO$_2$CH$_3$, —O$_{mm}$—(CH$_2$)$_{nn}$—CF$_3$, alkoxy having 1 to 4 carbon atoms, or alkyl having 1 to 4 carbon atoms, where mm is 0 to 1, nn is 0 to 3, and ll is 0 to 4; or (c) —(CH$_2$)$_{oo}$-heteroaryl which is unsubstituted or substituted by 1 to 3 radicals selected, each independently, from the group consisting of F, Cl, Br, I, —SO$_2$CH$_3$, —O$_{pp}$—(CH$_2$)$_{rr}$—CF$_3$, alkoxy having 1 to 4 carbon atoms or alkyl having 1 to 4 carbon atoms, where pp is 0 to 1, rr is 0 to 3, and oo is 0 to 4;

and salts thereof; excluding compounds of Formula (I) wherein, in the same molecule:

R2 and R4 are each Cl and R3 is F or Cl;
one of the R2 and R4 substituents is Cl and the other of the R2 and R4 substituents is CN and R3 is Cl; and
R1 is NO$_2$ and the other substituents are each hydrogen.

* * * * *